United States Patent
Kao et al.

(10) Patent No.: US 12,180,434 B2
(45) Date of Patent: *Dec. 31, 2024

(54) SPIRO COMPOUNDS AS MALODOR COUNTERACTING INGREDIENTS

(71) Applicant: Firmenich SA, Satigny (CH)

(72) Inventors: Huey-Ling Kao, Plainsboro, NJ (US); Stefan Alexander Ruider, Rumlang (CH); Steven Williams, Plainsboro, NJ (US); Julien Coulomb, Satigny (CH)

(73) Assignee: Firmenich SA, Satigny (CH)

( * ) Notice: Subject to any disclaimer, the term of this patent is extended or adjusted under 35 U.S.C. 154(b) by 1122 days.

This patent is subject to a terminal disclaimer.

(21) Appl. No.: 16/760,684

(22) PCT Filed: Nov. 21, 2018

(86) PCT No.: PCT/EP2018/082123
§ 371 (c)(1),
(2) Date: Apr. 30, 2020

(87) PCT Pub. No.: WO2019/101814
PCT Pub. Date: May 31, 2019

(65) Prior Publication Data
US 2023/0159853 A1    May 25, 2023

Related U.S. Application Data

(60) Provisional application No. 62/754,849, filed on Nov. 2, 2018, provisional application No. 62/589,841, filed on Nov. 22, 2017.

(30) Foreign Application Priority Data

Feb. 9, 2018   (EP) .................................... 18156134

(51) Int. Cl.
C11B 9/00          (2006.01)
C07C 49/297     (2006.01)
(Continued)

(52) U.S. Cl.
CPC ........... *C11B 9/0057* (2013.01); *C07C 49/297* (2013.01); *C07C 49/303* (2013.01); *C07C 49/537* (2013.01); *C07C 49/543* (2013.01)

(58) Field of Classification Search
None
See application file for complete search history.

(56) References Cited

U.S. PATENT DOCUMENTS 4,217,251 A * 8/1980 Dastur .................. A24B 15/34
512/8
5,268,356 A   12/1993 Decorzant et al.
(Continued)

FOREIGN PATENT DOCUMENTS

EP    3004157 B1    11/2017
JP    2015202076 A    11/2015
WO    2016/049455 A1    3/2016

OTHER PUBLICATIONS

"Macrocyclic Lactones and Ketones, Ionones and Cyclohexanone Group", May 2018, downloaded from: https://www.canada.ca/en/environment-climate-change/services/evaluating-existing-substances/screening-assessment-macrocylic-lactones-ketones-ionones-cyclohexanone-group.html on Oct. 30, 2023 (Year: 2018).*

(Continued)

*Primary Examiner* — Amy C Bonaparte
(74) *Attorney, Agent, or Firm* — Robert S. Dailey

(57) ABSTRACT

The various aspects presented herein relate to the perfumery industry. More particularly, the various aspects presented herein relate to malodor counteracting compositions and/or ingredients, methods for counteracting malodors, as well as (Continued)

to the perfumed articles or perfuming compositions comprising as an active ingredient, at least one compound selected from the group consisting of: a compound of Formula (I), a compound of Formula (II), a compound of Formula (III), a compound of Formula (IV), and mixtures thereof.

3 Claims, 17 Drawing Sheets

(51) Int. Cl.
*C07C 49/303* (2006.01)
*C07C 49/537* (2006.01)
*C07C 49/543* (2006.01)

(56) References Cited

U.S. PATENT DOCUMENTS

| | | | | |
|---|---|---|---|---|
| 11,744,785 | B2* | 9/2023 | Kao | A61K 8/34 |
| | | | | 424/76.1 |
| 2004/0072721 | A1 | 4/2004 | Alain et al. | |
| 2011/0050246 | A1 | 3/2011 | Kumihashi et al. | |
| 2012/0184630 | A1* | 7/2012 | Kraft | C07C 69/24 |
| | | | | 560/231 |
| 2014/0296120 | A1* | 10/2014 | Levorse, Jr. | A61Q 13/00 |
| | | | | 549/462 |
| 2016/0089313 | A1 | 3/2016 | Kato et al. | |
| 2022/0218860 | A1 | 7/2022 | Rogers et al. | |
| 2023/0159853 | A1* | 5/2023 | Kao | C07C 49/543 |
| | | | | 560/256 |

OTHER PUBLICATIONS

PubChem Compound Summary for CID 61771, 2-sec-Butylcyclohexanone. Retrieved Oct. 30, 2023 from https://pubchem.ncbi.nlm.nih.gov/compound/2-sec-Butylcyclohexanone (Year: 2023).*
Api ("RIFM fragrance ingredient safety assessment, 2,2,6-trimethylcyclohexanone, CAS Registry No. 2408-37-9" Food and Chemical Toxicology, 134, 2019, p. 110723) (Year: 2019).*
Szewczyk ("Comparison of the Essential Oil Composition of Selected Impatiens Species and Its Antioxidant Properties" Molecules, 2016, p. 1162) (Year: 2016).*
International Search Report and Written Opinion for International Application No. PCT/EP2018/082123 dated Sep. 13, 2019; 23 pages.

* cited by examiner

SPIRO COMPOUNDS AS MALODOR COUNTERACTING INGREDIENTS

CROSS REFERENCE TO RELATED APPLICATIONS

The present application claims priority to U.S. Provisional Patent Application Ser. No. 62/589,841, filed on Nov. 22, 2017, European Patent Application Serial No. 18156134.1, filed on Feb. 9, 2018, and U.S. Provisional Patent Application Ser. No. 62/754,849, filed on Nov. 2, 2018, the entire contents of which are hereby incorporated by reference in their entirety.

FIELD OF THE INVENTION

The various aspects presented herein relate to the perfumery industry. More particularly, the various aspects presented herein relate to malodor counteracting compositions and/or ingredients, methods for counteracting malodors, as well as to the perfumed articles or perfuming compositions comprising as an active ingredient, at least one compound selected from the group consisting of: a compound of Formula (I), a compound of Formula (II), a compound of Formula (III), a compound of Formula (IV), and mixtures thereof.

BACKGROUND

Malodorous smells exist in many environments and are experienced in our day life. Such odors are created in any environment. Malodorous smells include the commercial and residential environment malodors generated by, for example, waste products, trash receptacles, toilets, cat litter, and food handling and processing. Other examples include environmental sources, such as latrine or bathroom (including feces or urine), laundry, kitchen and body malodors. Malodors are frequently complex mixtures of more than one malodorant compound which may typically include various amines, thiols, sulfides, short chain aliphatic and olefinic acids, e.g. fatty acids, and derivatives thereof. For example, residential or body related malodors typically include indole, skatole, and methanethiol (found in feces malodor): piperidine and morpholine (found in urine): pyridine and triethyl amine (found in kitchen and garbage malodors); and short chain fatty acids, such as 3-methyl-3-hydroxyhexanoic acid, 3-methylhexanoic acid or 3-20 methyl-2-hexenoic acid, (found in axilla malodors).

Malodors are not pleasant for humans and therefore there is a constant need for malodor counteracting (MOC) compositions and/or ingredients for decreasing or suppressing the perception of malodors. Various approaches exist to achieve such goal with MOC compositions and/or ingredients, and include masking, which relates to the suppression or decrease of the perception of a malodor by various mechanisms such as, for example by the MOC compositions and/or ingredients having an olfactory receptor antagonist activity.

The present disclosure provides MOC compositions and/or ingredients comprising compounds that are capable of antagonizing specific receptors of malodor targets.

SUMMARY

One aspect presented herein provides a method, wherein the method reduces, prevents, or inhibits a subject's perception of malodor, wherein the method comprises contacting the subject with at least one compound selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl) acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl) acetate, (9,9-dimethylspiro[4.5]dec-2-en-10-yl) acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol[2,2-dimethyl-1-(2,4,6-trimethylcyclohex-3-en-1-yl) propyl]acetate, [2,2-dimethyl-1-(2,4,6-trimethylcyclohexyl) propyl]acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], 4,9,9-trimethylspiro[4.5]dec-2-en-10-one, 2,2-dimethyl-6,6-bis(2-methylprop-2-enyl) cyclohexan-1-one, 2,2-dimethyl-5,5-bis(2-methylprop-2-enyl) cyclopentan-1-one, 2-but-3-en-2-yl-6,6-dimethyl-2-prop-2-enylcyclohexan-1-one, 2,2-bis(2-methyl-2-propen-1-yl) cyclohexanone, a mixture of 2-but-3-en-2-yl-6,6-dimethyl-2-prop-2-enylcyclohexan-1-one and 2,2-bis(2-methyl-2-propen-1-yl) cyclohexanone, 2,2-dimethyl-1-(2-methylcyclohexyl) propan-1-ol, 2,2-dimethyl-1-(3-methylcyclohexyl) propan-1-ol, a mixture of 2,2-dimethyl-1-(2-methylcyclohexyl) propan-1-ol and 2,2-dimethyl-1-(3-methylcyclohexyl) propan-1-ol, 2,2-dimethyl-6,6-bis(2-methylprop-2-enyl) cyclohexan-1-ol, 1-methoxy-2,6-dimethyl-1-prop-2-enylcyclohexane, methyl 1-(3-methylbut-2-enyl) cyclohex-2-ene-1-carboxylate, methyl 1-(3-methylbut-2-enyl) cyclohex-3-ene-1-carboxylate, a mixture of methyl 1-(3-methylbut-2-enyl) cyclohex-2- ene-1-carboxylate and methyl 1-(3-methylbut-2-enyl) cyclohex-3-ene-1-carboxylate, 2,2-dimethyl-5,5-bis(2-methylprop-2-enyl) cyclopentan-1-ol, 1-(2,6-dimethyl-cyclohex-3-en-1-yl)-2,2-dimethylpropan-1-ol, and mixtures thereof, wherein the subject is contacted with the at least one compound in an amount sufficient to reduce, prevent, or inhibit the subject's perception of malodor.

In one aspect, the malodor contains butyric acid.

In one aspect, the malodor is selected from the group consisting of: latrine malodor, laundry malodor, and sweat malodor.

In one aspect, the amount sufficient to reduce, prevent, or inhibit the subject's perception of malodor inhibits at least one olfactory malodor receptor in the subject.

In one aspect, the at least one olfactory malodor receptor is a butyric acid olfactory receptor.

One aspect presented herein provides a method
wherein the method inhibits at least one butyric acid receptor in a subject in need thereof,
wherein the method comprises contacting the subject with at least one compound selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl) acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl) acetate, (9,9-dimethylspiro[4.5]dec-2-en-10-yl) acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol, [2,2-dimethyl-1-(2,4,6-trimethylcyclohex-3-en-1-yl) propyl]acetate, [2,2-dimethyl-1-(2,4,6-trimethylcyclohexyl) propyl]acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], 4,9,9-trimethylspiro[4.5]dec-2-en-10-one, 2,2-dimethyl-6,6-bis(2-methylprop-2-enyl) cyclohexan-1-one, 2,2-dimethyl-5,5-bis(2-methylprop-2-enyl) cyclopentan-1-one, 2-but-3-en-2-yl-6,6-dimethyl-2-prop-2-enylcyclohexan-1-one, 2,2-bis(2-methyl-2-propen-1-yl) cyclohexanone, a mixture of 2-but-3-en-2-yl-6,6-dimethyl-2-prop-2-enylcyclohexan-1-one and 2,2-bis(2-methyl-2-propen-1-yl) cyclohexanone, 2,2-dimethyl-1-(2-methylcyclohexyl) propan-1-ol, 2,2-dimethyl-1-(3-methylcyclohexyl) propan-1-ol, a mixture of 2,2-dimethyl-1-(2-methylcyclohexyl) propan-1-ol and 2,2-dimethyl-1-(3-methylcyclohexyl) propan-1-ol, 2,2-dimethyl-6,6-bis(2-methylprop-2-enyl) cyclohexan-1-ol, 1-methoxy-2,6-dimethyl-1-prop-2-enylcyclohexane, methyl 1-(3-methylbut-2-enyl) cyclohex-2-ene-1-carboxylate, methyl 1-(3-methylbut-2-enyl) cyclohex-3-ene-1-carboxylate, a mixture of methyl 1-(3-methylbut-2-enyl) cyclohex-2-ene-1-carboxylate and methyl 1-(3-methylbut-2-enyl) cyclohex-3-ene-1-carboxylate, 2,2-dimethyl-5,5-bis(2-methylprop-2-enyl) cyclopentan-1-ol, 1-(2,6-dimethyl-cyclohex-3-en-1-yl)-2,2-dimethylpropan-1-ol, and mixtures thereof, wherein the subject is contacted with the at least one compound in an amount sufficient to inhibit the at least one butyric acid receptor.

In one aspect, inhibition of the at least one butyric acid olfactory receptor inhibits, reduces, suppresses, or inhibits the perception of a malodor in the subject.

In one aspect, the malodor comprises butyric acid.

In one aspect, the malodor is selected from the group consisting of: latrine malodor, laundry malodor, and sweat malodor.

One aspect presented herein provides a compound having the structure:

Formula (I)

in a form of any one of the stereoisomers or as a mixture thereof wherein the index m represents 0 or 1;

wherein the index n represents 1 or 2;

wherein the dotted lines represent a single or a double bond;

wherein $R^1$ represents a hydrogen atom, a methyl group or a $R^6C(=O)$ group wherein $R^6$ represents a hydrogen atom or a methyl, ethyl, propyl or isopropyl group;

wherein $R^2$, $R^3$ and $R^4$ represent, independently from each other, a hydrogen atom or a methyl group;

wherein each $R^5$ represent, independently from each other, a hydrogen atom or a $C_{1-3}$ alkyl or alkenyl group; and wherein the compound of Formula (I) is an antagonist of a butyric acid olfactory receptor.

In one aspect, the compound of Formula (I) is selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl) acetate, (9,9-dimethylspiro[4.5]dec-2-en-10-yl) acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-yl-spiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol, [2,2-dimethyl-1-(2,4,6-trimethylcyclohex-3-en-1-yl) propyl]acetate, [2,2-dimethyl-1-(2,4,6-trimethylcyclohexyl) propyl]acetate, (1RS)-2,2-dimethyl-1-[(1SR,2SR)-2-methylcyclohexyl] propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, and (4~{S},5~{R},6~{S},11~{S})-4,11-dimethylspiro[5.5]undecan-5-ol.

In one aspect, the compound of Formula (I) is selected from the group consisting of: (+−)-2,3,7,7-tetramethylspiro[4.5]dec-2-en-6-yl acetate, (+−)-2,3,7,7-tetramethylspiro[4.5]dec-6-yl acetate, (9,9-dimethylspiro[4.5]dec-2-en-10-yl) acetate, and 10-methoxy-9,9-dimethylspiro[4.5]dec-2-ene.

One aspect presented herein provides a compound having the structure:

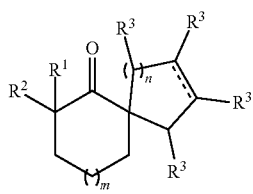

Formula (II)

in a form of any one of the stereoisomers or as a mixture thereof
wherein the index m represents 0 or 1;
wherein the index n represents 1 or 2;
wherein the dotted lines represent a single or a double bond;
wherein $R^1$, and $R^2$ represent, independently from each other, a hydrogen atom or a methyl group;
wherein each $R^3$ represent, independently from each other, a hydrogen atom or a $C_{1-3}$ alkyl or alkenyl group; and
wherein the compound of Formula (II) is an antagonist of a butyric acid olfactory receptor.

In one aspect, the compound of Formula (II) is selected from the group consisting of: 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], and 4,9,9-trimethylspiro[4.5]dec-2-en-10-one.

One aspect presented herein provides a compound having the structure:

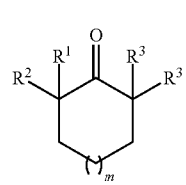

Formula (III)

in a form of any one of the stereoisomers or as a mixture thereof
wherein the index m represents 0 or 1;
wherein $R^1$, and $R^2$ represent, independently from each other, a hydrogen atom or a methyl group;
wherein each $R^3$ represent, independently from each other, a hydrogen atom or a $C_{1-4}$ alkyl or alkenyl group; and
wherein the compound of Formula (III) is an antagonist of a butyric acid olfactory receptor.

In one aspect, the compound of Formula (III) is selected from the group consisting of: 2,2-dimethyl-6,6-bis(2-methylprop-2-enyl) cyclohexan-1-one, 2,2-dimethyl-5,5-bis(2-methylprop-2-enyl) cyclopentan-1-one, 2-but-3-en-2-yl-6,6-dimethyl-2-prop-2-enylcyclohexan-1-one, and 2,2-bis(2-methyl-2-propen-1-yl) cyclohexanone.

One aspect presented herein provides a compound having the structure:

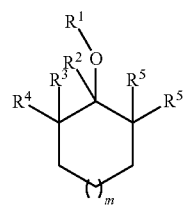

Formula (IV)

in a form of any one of the stereoisomers or as a mixture thereof
wherein the index m represents 0 or 1;
wherein $R^1$ represents a hydrogen atom, a methyl group or a $R^6C(=O)$ group wherein $R^6$ represents a hydrogen atom or a methyl, ethyl, propyl or isopropyl group;
wherein $R^2$, $R^3$ and $R^4$ represent, independently from each other, a hydrogen atom, a methyl group, a $C_{1-4}$ alkyl or alkenyl group;

wherein each $R^5$ represent, independently from each other, a hydrogen atom or a $C_{1-4}$ alkyl or alkenyl group; and wherein the compound of Formula (IV) is an antagonist of a butyric acid olfactory receptor.

In one aspect, the compound of Formula (IV) is selected from the group consisting of: 2,2-dimethyl-1-(2-methylcyclohexyl) propan-1-ol, 2,2-dimethyl-1-(3-methylcyclohexyl) propan-1-ol, a mixture of 2,2-dimethyl-1-(2-methylcyclohexyl) propan-1-ol and 2,2-dimethyl-1-(3-methylcyclohexyl) propan-1-ol, 2,2-dimethyl-6,6-bis(2-methylprop-2-enyl) cyclohexan-1-ol, 1-methoxy-2,6-dimethyl-1-prop-2-enylcyclohexane, methyl 1-(3-methylbut-2-enyl) cyclohex-2-ene-1-carboxylate, methyl 1-(3-methylbut-2-enyl) cyclohex-3-ene-1-carboxylate, a mixture of methyl 1-(3-methylbut-2-enyl) cyclohex-2-ene-1-carboxylate, and methyl 1-(3-methylbut-2-enyl) cyclohex-3-ene-1-carboxylate, and 2,2-dimethyl-5,5-bis(2-methylprop-2-enyl) cyclopentan-1-ol.

One aspect presented herein provides a perfuming composition comprising at least one compound selected from the group consisting of: a compound of Formula (I), a compound of Formula (II), a compound of Formula (III), a compound of Formula (IV), and mixtures thereof.

One aspect presented herein provides a consumer product comprising at least one compound selected from the group consisting of: a compound of Formula (I), a compound of Formula (II), a compound of Formula (III), a compound of Formula (IV), and mixtures thereof.

One aspect presented herein provides a method,
wherein the method reduces, prevents, or inhibits a subject's perception of malodor,
wherein the method comprises contacting the subject with at least one compound selected from the group consisting of: a compound of Formula (I), a compound of Formula (II), a compound of Formula (III), a compound of Formula (IV), and mixtures thereof,
wherein the subject is contacted with the at least one compound selected from the group consisting of: a compound of Formula (I), a compound of Formula (II), a compound of Formula (III), a compound of Formula (IV), and mixtures thereof in an amount sufficient to reduce, prevent, or inhibit the subject's perception of malodor.

In one aspect, the malodor contains butyric acid.

In one aspect, the malodor is selected from the group consisting of: latrine malodor, laundry malodor, and sweat malodor.

In one aspect, the amount sufficient to reduce, prevent, or inhibit the subject's perception of malodor inhibits at least one olfactory malodor receptor in the subject.

In one aspect, the at least one olfactory malodor receptor is a butyric acid olfactory receptor.

One aspect presented herein provides a method
wherein the method inhibits at least one butyric acid receptor in a subject in need thereof,
wherein the method comprises contacting the subject with at least one compound selected from the group consisting of: a compound of Formula (I), a compound of Formula (II), a compound of Formula (III), a compound of Formula (IV), and mixtures thereof,
wherein the subject is contacted with the at least one compound selected from the group consisting of: a compound of Formula (I), a compound of Formula (II), a compound of Formula (III), a compound of Formula (IV), and mixtures thereof in an amount sufficient to inhibit the at least one butyric acid receptor.

In one aspect, inhibition of the at least one butyric acid olfactory receptor inhibits, reduces, suppresses, or inhibits the perception of a malodor in the subject.

In one aspect, the malodor comprises butyric acid.

In one aspect, the malodor is selected from the group consisting of: latrine malodor, laundry malodor, and sweat malodor.

DETAILED DESCRIPTION

Figure 1:
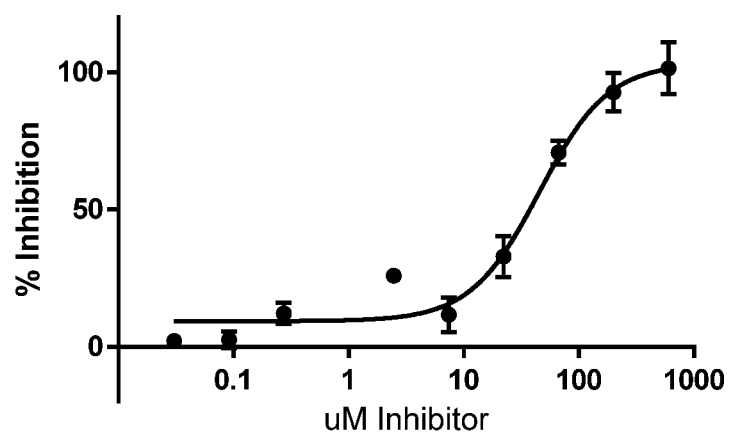
FIG. 1 shows the potency of the antagonist (1RS,6RS,11RS)-2,2,9,11-tetramethylspiro[5.5]undec-8-en-1-yl acetate (Compound 1) as an inhibitor of the butyric acid olfactory receptor OR51E1 under highly stringent screening conditions. The black line denotes the % inhibition of the butyric acid olfactory receptor activity observed from cells treated with 67 μM butyric acid ($EC_{94}$) and the antagonist at the concentrations indicated. The calculated $IC_{50}$ of Compound 1 under these conditions was 45.18 μM.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72 (b) to allow the reader to quickly ascertain the nature and gist of the technical disclosure. The Abstract is submitted with the understanding that it will not be used to interpret or limit the scope or meaning of the claims.

Compounds According to Some Aspects of the Present Disclosure

Some aspects described herein provide a compound having the structure:

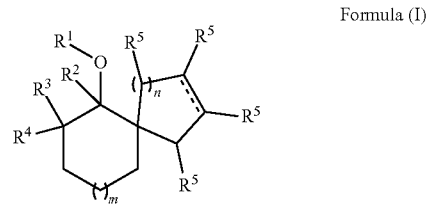

Formula (I)

in a form of any one of the stereoisomers or as a mixture thereof
wherein the index m represents 0 or 1;
wherein the index n represents 1 or 2;
wherein the dotted lines represent a single or a double bond;
wherein $R^1$ represents a hydrogen atom, a methyl group or a $R^6C(=O)$ group
wherein $R^6$ represents a hydrogen atom or a methyl, ethyl, propyl or isopropyl group;
wherein $R^2$, $R^3$ and $R^4$ represent, independently from each other, a hydrogen atom or a methyl group;
wherein each $R^5$ represent, independently from each other, a hydrogen atom or a $C_{1-3}$ alkyl or alkenyl group; and
wherein the compound of Formula (I) is an antagonist of a butyric acid olfactory receptor.

For the sake of clarity, by the expression "any one of its stereoisomers", or the similar, it is meant the normal meaning understood by a person skilled in the art, i.e. that the invention compounds can be a pure or be in the form of a mixture of enantiomers or diastereoisomers.

For the sake of clarity, by the expression "wherein the dotted line represents a carbon-carbon single or a carbon-carbon double bond", or the similar, it is meant the normal meaning understood by a person skilled in the art, i.e. that the whole bonding (solid and dotted line) between the carbon atoms connected by said dotted line is a carbon-carbon single or double bond.

In some aspects, $R^2$ may be a hydrogen atom.
In some aspects, $R^3$ may be a methyl group.
In some aspects, $R^4$ may be a methyl group.
In some aspects, the index m may be 1.
In some aspects, the index n may be 1.
In some aspects, the dotted line may represent a double bond.
In some aspects, $R^1$ may represent a hydrogen atom or a $R^6C(=O)$ group wherein $R^6$ represents a hydrogen atom or a methyl group.
In some aspects, $R^1$ may represent a $R^6C(=O)$ group wherein $R^6$ represents a hydrogen atom or a methyl group.
In some aspects, $R^1$ may represent a $CH_3C(=O)$.
In some aspects: each $R^5$ may represent, independently from each other, a hydrogen atom or a $C_{1-3}$ alkyl group.
In some aspects: each $R^5$ may represent, independently from each other, a hydrogen atom or a methyl or ethyl group.
In some aspects: each $R^5$ may represent, independently from each other, a hydrogen atom or a methyl group.
In some aspects: one or two $R^5$ may represent a methyl group and the other a hydrogen atom.

In some aspects, the compound of Formula (I) is selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl) acetate, (9,9-dimethylspiro[4.5]dec-2-en-10-yl) acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-yl-spiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol, [2,2-dimethyl-1-(2,4,6-trimethylcyclohex-3-en-1-yl) propyl]acetate, [2,2-dimethyl-1-(2,4,6-trimethylcyclohexyl) propyl]acetate, (1RS)-2,2-dimethyl-1-[(1SR,2SR)-2-methylcyclohexyl] propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, and (4~{S},5~{R},6~{S},11~{S})-4,11-dimethylspiro[5.5]undecan-5-ol.

In some aspects, the compound of Formula (I) is selected from the group consisting of: (+−)-2,3,7,7-tetramethylspiro[4.5]dec-2-en-6-yl acetate, (+−)-2,3,7,7-tetramethylspiro[4.5]dec-6-yl acetate, (9,9-dimethylspiro[4.5]dec-2-en-10-yl) acetate, and 10-methoxy-9,9-dimethylspiro[4.5]dec-2-ene.

In some aspects, the compound of Formula (I) has the structure:

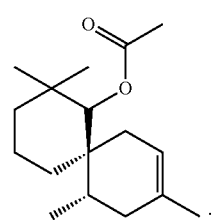

(Compound 1)

In some aspects, the compound of Formula (I) has the structure:

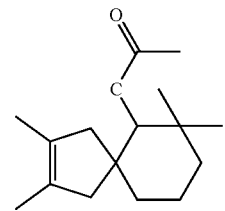

(Compound 2)

In some aspects, the compound of Formula (I) has the structure:

(Compound 3)

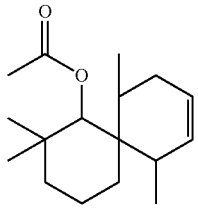

In some aspects, the compound of Formula (I) has the structure:

(Compound 4)

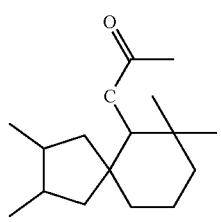

In some aspects, the compound of Formula (I) has the structure:

(Compound 5)

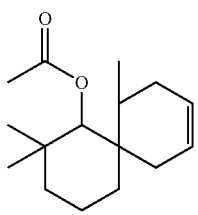

In some aspects, the compound of Formula (I) has the structure:

(Compound 6)

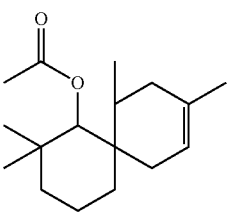

In some aspects, the compound of Formula (I) has the structure:

(Compound 7)

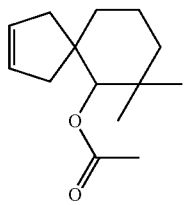

In some aspects, the compound of Formula (I) has the structure:

(Compound 8)

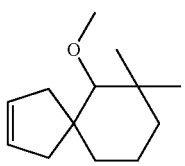

In some aspects, the compound of Formula (I) has the structure:

(Compound 9)

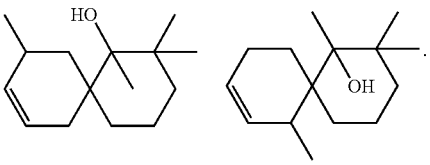

In some aspects, the compound of Formula (I) has the structure:

(Compound 10)

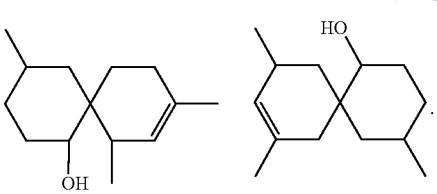

In some aspects, the compound of Formula (I) has the structure:

(Compound 11)

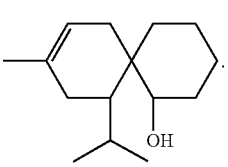

In some aspects, the compound of Formula (I) has the structure:

(Compound 12)

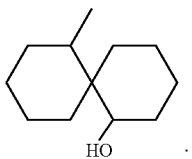

In some aspects, the compound of Formula (I) has the structure:

(Compound 13)

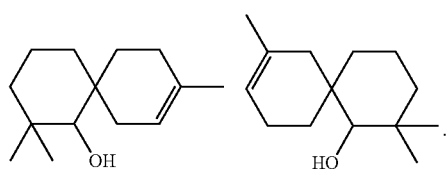

In some aspects, the compound of Formula (I) has the structure:

(Compound 18)

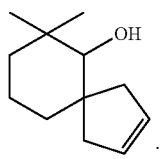

In some aspects, the compound of Formula (I) has the structure:

(Compound 19)

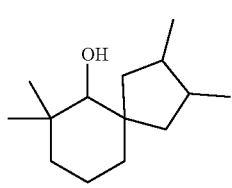

In some aspects, the compound of Formula (I) has the structure:

(Compound 21)

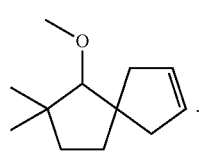

In some aspects, the compound of Formula (I) has the structure:

(Compound 22)

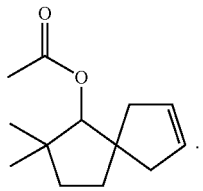

In some aspects, the compound of Formula (I) has the structure:

(Compound 24)

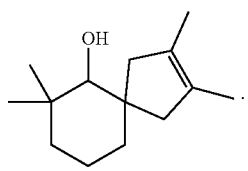

In some aspects, the compound of Formula (I) has the structure:

(Compound 25)

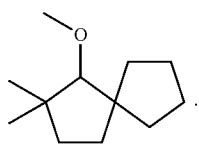

In some aspects, the compound of Formula (I) has the structure:

(Compound 26)

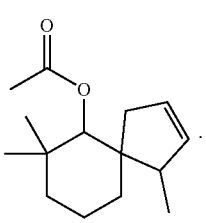

In some aspects, the compound of Formula (I) has the structure:

(Compound 27)

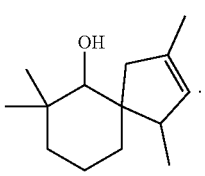

In some aspects, the compound of Formula (I) has the structure:

(Compound 28)

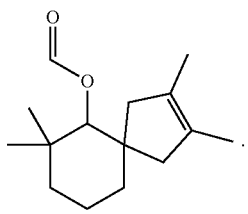

In some aspects, the compound of Formula (I) has the structure:

(Compound 29)

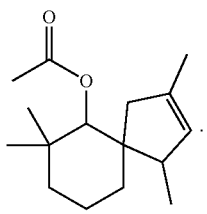

In some aspects, the compound of Formula (I) has the structure:

(Compound 30)

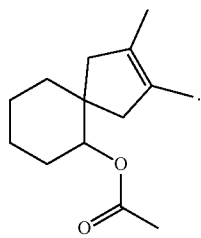

In some aspects, the compound of Formula (I) has the structure:

(Compound 31)

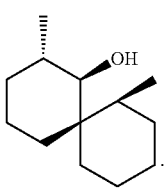

In some aspects, the compound of Formula (I) is selected from the compounds disclosed in U.S. Pat. No. 7,256,170 B2.

In some aspects, the compound of Formula (I) is an antagonist of a butyric acid olfactory receptor.

Some aspects presented herein provide a compound having the structure:

Formula (II)

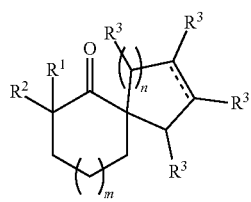

in a form of any one of the stereoisomers or as a mixture thereof wherein the index m represents 0 or 1;

wherein the index n represents 1 or 2;

wherein the dotted lines represent a single or a double bond;

wherein $R^1$, and $R^2$ represent, independently from each other, a hydrogen atom or a methyl group;

wherein each $R^3$ represent, independently from each other, a hydrogen atom or a $C_{1-3}$ alkyl or alkenyl group; and wherein the compound of Formula (II) is an antagonist of a butyric acid olfactory receptor.

In some aspects, the compound of Formula (II) is selected from the group consisting of: 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], and 4,9,9-trimethylspiro[4.5]dec-2-en-10-one.

In some aspects, the compound of Formula (II) has the structure:

(Compound 23)

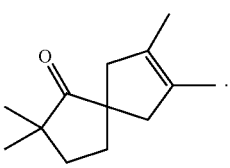

In some aspects, the compound of Formula (II) has the structure:

(Compound 32)

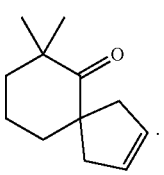

In some aspects, the compound of Formula (II) has the structure:

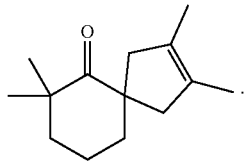
(Compound 33)

In some aspects, the compound of Formula (II) has the structure:

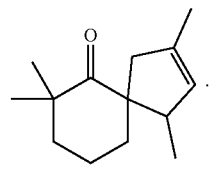
(Compound 34)

In some aspects, the compound of Formula (II) has the structure:

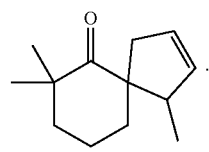
(Compound 36)

In some aspects, the compound of Formula (II) is an antagonist of a butyric acid olfactory receptor.

Some aspects presented herein provide a compound having the structure:

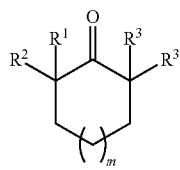
Formula (III)

in a form of any one of the stereoisomers or as a mixture thereof
wherein the index m represents 0 or 1;
wherein $R^1$, and $R^2$ represent, independently from each other, a hydrogen atom or a methyl group;
wherein each $R^3$ represent, independently from each other, a hydrogen atom or a $C_{1-4}$ alkyl or alkenyl group; and
wherein the compound of Formula (III) is an antagonist of a butyric acid olfactory receptor.

In some aspects, the compound of Formula (III) is selected from the group consisting of: 2,2-dimethyl-6,6-bis(2-methylprop-2-enyl) cyclohexan-1-one, 2,2-dimethyl-5,5-bis(2-methylprop-2-enyl) cyclopentan-1-one, 2-but-3-en-2-yl-6,6-dimethyl-2-prop-2-enylcyclohexan-1-one, a mixture of 2,2-dimethyl-5,5-bis(2-methylprop-2-enyl) cyclopentan-1-one and 2-but-3-en-2-yl-6,6-dimethyl-2-prop-2-enylcyclohexan-1-one, and 2,2-bis(2-methyl-2-propen-1-yl) cyclohexanone.

In some aspects, the compound of Formula (III) has the structure:

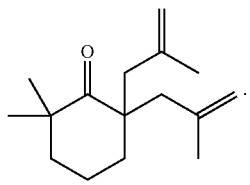
(Compound 37)

In some aspects, the compound of Formula (III) has the structure:

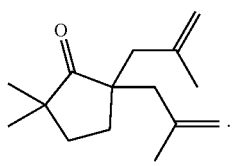
(Compound 38)

In some aspects, the compound of Formula (III) has the structure:

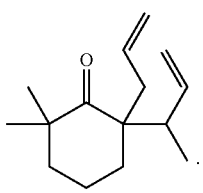
(Compound 39)

In some aspects, the compound of Formula (III) has the structure:

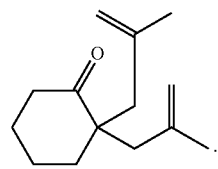
(Compound 40)

In some aspects, the compound of Formula (III) is an antagonist of a butyric acid olfactory receptor.

Some aspects presented herein provide a compound having the structure:

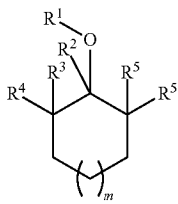

Formula (IV)

in a form of any one of the stereoisomers or as a mixture thereof wherein the index m represents 0 or 1;

wherein $R^1$ represents a hydrogen atom, a methyl group or a $R^6C(=O)$ group wherein $R^6$ represents a hydrogen atom or a methyl, ethyl, propyl or isopropyl group;

wherein $R^2$, $R^3$ and $R^4$ represent, independently from each other, a hydrogen atom, a methyl group, a $C_{1-4}$ alkyl or alkenyl group;

wherein each $R^5$ represent, independently from each other, a hydrogen atom or a $C_{1-4}$ alkyl or alkenyl group; and wherein the compound of Formula (IV) is an antagonist of a butyric acid olfactory receptor.

In some aspects, the compound of Formula (IV) is selected from the group consisting of: 2,2-dimethyl-1-(2-methylcyclohexyl) propan-1-ol, 2,2-dimethyl-1-(3-methylcyclohexyl) propan-1-ol, a mixture of 2,2-dimethyl-1-(2-methylcyclohexyl) propan-1-ol and 2,2-dimethyl-1-(3-methylcyclohexyl) propan-1-ol, 2,2-dimethyl-6,6-bis(2-methylprop-2-enyl) cyclohexan-1-ol, 1-methoxy-2,6-dimethyl-1-prop-2-enylcyclohexane, methyl 1-(3-methylbut-2-enyl) cyclohex-2-ene-1-carboxylate, methyl 1-(3-methylbut-2-enyl) cyclohex-3-ene-1-carboxylate, a mixture of methyl 1-(3-methylbut-2-enyl) cyclohex-2-ene-1-carboxylate and methyl 1-(3-methylbut-2-enyl) cyclohex-3-ene-1-carboxylate, and 2,2-dimethyl-5,5-bis(2-methylprop-2-enyl) cyclopentan-1-ol.

In some aspects, the compound of Formula (IV) has the structure:

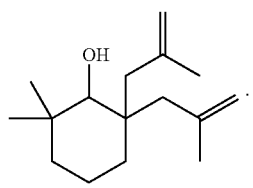

(Compound 42)

In some aspects, the compound of Formula (IV) has the structure:

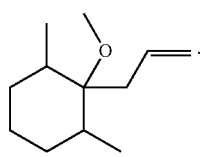

(Compound 43)

In some aspects, the compound of Formula (IV) is an antagonist of a butyric acid olfactory receptor.

The terms "antagonists," "inhibitor," "blockers," "suppressors," "counteractants" and "modulators" of olfactory receptors are used interchangeably to refer to inhibitory, blocking, suppressing, or modulating molecules identified using in vivo, ex vivo and in vitro assays for olfactory transduction, e.g., ligands, antagonists, and their homologs and mimetics. Inhibitors are compounds that, e.g., bind to, partially or totally block stimulation, decrease, suppress, prevent, delay activation, inactivate, desensitize, or down regulate olfactory transduction, e.g., antagonists. Activators are compounds that, e.g., bind to, stimulate, increase, open activate, facilitate, enhance activation, sensitize, or up regulate olfactory transduction, e.g., agonists. Modulators include compounds that, e.g., alter the interaction of a receptor with: extracellular proteins that bind activators or inhibitor (e.g., odorant-binding proteins, ebnerin and other members of the hydrophobic carrier family): G proteins: kinases (e.g., homologs of rhodopsin kinase and beta adrenergic receptor kinases that are involved in deactivation and desensitization of a receptor); and arrestins, which also deactivate and desensitize receptors.

The ability of compounds of the present disclosure to inhibit or antagonize a butyric acid olfactory receptor may be determined by any suitable method readily selected by one of ordinary skill in the art, such as, for example, via an ex vivo cultured neuron assay, or via an in vitro assay using a cell line that expresses a butyric acid olfactory receptor.

Such assays for inhibitors and activators include, e.g., expressing OR family members in cells or cell membranes, applying putative modulator compounds, in the presence or absence of malodor molecules, e.g. butyric acid, and then determining the functional effects on olfactory transduction, as described in the Examples below. Samples or assays comprising OR family members that are treated with a potential inhibitor are compared to control samples without the inhibitor to examine the extent of inhibition. Control samples (untreated with inhibitors, but treated with the malodor) are assigned a relative maximal OR activity value of 100%. Inhibition of an OR is achieved when the normalized OR activity value relative to the control is about 80%, optionally 50% or 25-0%. Alternatively, in some aspects, inhibition of an OR is achieved if the $IC_{50}$ value of the antagonist compound is equal to or less than 1000 µM. Alternatively, in some aspects, inhibition of an OR is achieved if the $IC_{50}$ value of the antagonist compound is equal to or less than 200 µM. Alternatively, in some aspects, inhibition of an OR is achieved if the $IC_{50}$ value of the antagonist compound is equal to or less than 20 µM.

As used herein, the term "olfactory receptor", or "OR" refers to one or more members of a family of G protein-coupled receptors (GPCRs) that are expressed in olfactory cells. Olfactory receptor cells can also be identified on the basis of morphology or by the expression of proteins specifically expressed in olfactory cells. OR family members may have the ability to act as receptors for odorants and induce an olfactory transduction cascade.

As used herein, the term "butyric acid olfactory receptor" refers to an olfactory receptor that is activated by butyric acid.

Non-limiting examples of butyric acid olfactory receptors suitable for inhibition by compounds of the present disclosure include: Olfr558 and OR51E1.

In some aspects, the compounds of the present disclosure have an $IC_{50}$ for the butyric acid olfactory receptor from 4 to 1000 µM. In some aspects, the compounds of the present disclosure have an IC$_{50}$ for the butyric acid olfactory receptor from 4 to 200 µM. In some aspects, the compounds of the present disclosure have an IC$_{50}$ for the butyric acid olfactory receptor from 4 to 20 µM.

In some aspects, the compounds of the present disclosure have an IC$_{50}$ for the butyric acid olfactory receptor from 6 to 200 µM. In some aspects, the compounds of the present disclosure have an IC$_{50}$ for the butyric acid olfactory receptor from 8 to 200 µM. In some aspects, the compounds of the present disclosure have an IC$_{50}$ for the butyric acid olfactory receptor from 10 to 200 µM. In some aspects, the compounds of the present disclosure have an IC$_{50}$ for the butyric acid olfactory receptor from 20 to 200 µM. In some aspects, the compounds of the present disclosure have an IC$_{50}$ for the butyric acid olfactory receptor from 30 to 200 µM. In some aspects, the compounds of the present disclosure have an IC$_{50}$ for the butyric acid olfactory receptor from 40 to 200 µM. In some aspects, the compounds of the present disclosure have an IC$_{50}$ for the butyric acid olfactory receptor from 50 to 200 µM. In some aspects, the compounds of the present disclosure have an IC$_{50}$ for the butyric acid olfactory receptor from 60 to 200 µM. In some aspects, the compounds of the present disclosure have an IC$_{50}$ for the butyric acid olfactory receptor from 70 to 200 µM. In some aspects, the compounds of the present disclosure have an IC$_{50}$ for the butyric acid olfactory receptor from 80 to 200 µM. In some aspects, the compounds of the present disclosure have an IC$_{50}$ for the butyric acid olfactory receptor from 90 to 200 µM. In some aspects, the compounds of the present disclosure have an IC$_{50}$ for the butyric acid olfactory receptor from 100 to 200 µM. In some aspects, the compounds of the present disclosure have an IC$_{50}$ for the butyric acid olfactory receptor from 120 to 200 µM. In some aspects, the compounds of the present disclosure have an IC$_{50}$ for the butyric acid olfactory receptor from 140 to 200 µM. In some aspects, the compounds of the present disclosure have an IC$_{50}$ for the butyric acid olfactory receptor from 160 to 200 µM. In some aspects, the compounds of the present disclosure have an IC$_{50}$ for the butyric acid olfactory receptor from 180 to 200 µM.

In some aspects, the compounds of the present disclosure have an IC$_{50}$ for the butyric acid olfactory receptor from 4 to 180 µM. In some aspects, the compounds of the present disclosure have an IC$_{50}$ for the butyric acid olfactory receptor from 4 to 160 µM. In some aspects, the compounds of the present disclosure have an IC$_{50}$ for the butyric acid olfactory receptor from 4 to 140 µM. In some aspects, the compounds of the present disclosure have an IC$_{50}$ for the butyric acid olfactory receptor from 4 to 120 µM. In some aspects, the compounds of the present disclosure have an IC$_{50}$ for the butyric acid olfactory receptor from 4 to 100 µM. In some aspects, the compounds of the present disclosure have an IC$_{50}$ for the butyric acid olfactory receptor from 4 to 90 µM. In some aspects, the compounds of the present disclosure have an IC$_{50}$ for the butyric acid olfactory receptor from 4 to 80 µM. In some aspects, the compounds of the present disclosure have an IC$_{50}$ for the butyric acid olfactory receptor from 4 to 70 µM. In some aspects, the compounds of the present disclosure have an IC$_{50}$ for the butyric acid olfactory receptor from 4 to 60 µM. In some aspects, the compounds of the present disclosure have an IC$_{50}$ for the butyric acid olfactory receptor from 4 to 50 µM. In some aspects, the compounds of the present disclosure have an IC$_{50}$ for the butyric acid olfactory receptor from 4 to 40 µM. In some aspects, the compounds of the present disclosure have an IC$_{50}$ for the butyric acid olfactory receptor from 4 to 30 µM. In some aspects, the compounds of the present disclosure have an IC$_{50}$ for the butyric acid olfactory receptor from 4 to 20 µM. In some aspects, the compounds of the present disclosure have an IC$_{50}$ for the butyric acid olfactory receptor from 4 to 10 µM. In some aspects, the compounds of the present disclosure have an IC$_{50}$ for the butyric acid olfactory receptor from 4 to 9 µM. In some aspects, the compounds of the present disclosure have an IC$_{50}$ for the butyric acid olfactory receptor from 4 to 8 µM. In some aspects, the compounds of the present disclosure have an IC$_{50}$ for the butyric acid olfactory receptor from 4 to 7 µM. In some aspects, the compounds of the present disclosure have an IC$_{50}$ for the butyric acid olfactory receptor from 4 to 6 µM. In some aspects, the compounds of the present disclosure have an IC$_{50}$ for the butyric acid olfactory receptor from 4 to 5 µM.

In some aspects, the compounds of the present disclosure have an IC$_{50}$ for the butyric acid olfactory receptor of 4, or 5, or 6, or 7, or 8, or 9, or 10, or 20, or 30, or 40, or 50, or 60, or 70, or 80, or 90, or 100, or 120, or 140, or 160, or 180, or 200 µM.

In some aspects, the following compound is an inhibitor of the at least one butyric acid olfactory receptor.

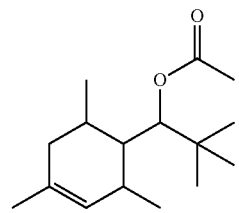

(Compound 14)

([2,2-dimethyl-1-(2,4,6-trimethylcyclohex-3-en-1-yl)propyl] acetate.

In some aspects, the following compound is an inhibitor of the at least one butyric acid olfactory receptor.

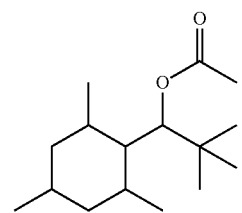

(Compound 15)

[2,2-dimethyl-1-(2,4,6-trimethylcyclohexyl)propyl] acetate.

In some aspects, the following compound is an inhibitor of the at least one butyric acid olfactory receptor.

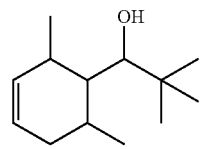

(Compound 16)

1-(2,6-dimethylcyclohex-3-en-1-yl)-2,2-dimethylpropan-1-ol

In some aspects, the following compound is an inhibitor of the at least one butyric (Compound 17)

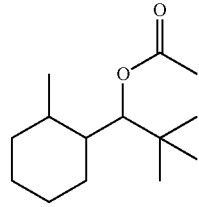

(IRS)-2,2-dimethyl-1-[(1SR,2SR)-2-methylcyclohexyl]propyl acetate.

In some aspects, the following compound is an inhibitor of the at least one butyric acid olfactory receptor.

(Compound 18)

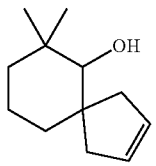

9,9-dimethylspiro[4.5]dec-2-en-10-ol.

In some aspects, the following compound is an inhibitor of the at least one butyric acid olfactory receptor.

(Compound 19)

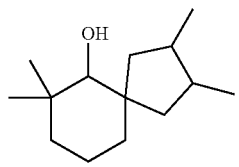

2,3,9,9-tetramethylspiro[4.5]decan-10-ol.

In some aspects, the following compound is an inhibitor of the at least one butyric acid olfactory receptor.

(Compound 20)

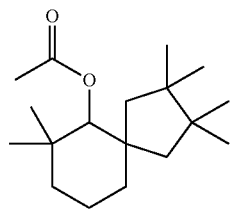

(2,2,3,3,9,9-hexamethylspiro[4.5]decan-10-yl) acetate

In some aspects, the following compound is an inhibitor of the at least one butyric acid olfactory receptor.

(Compound 21)

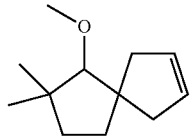

9-methoxy-8,8-dimethylspiro[4.4]non-2-ene

In some aspects, the following compound is an inhibitor of the at least one butyric acid olfactory receptor.

(Compound 22)

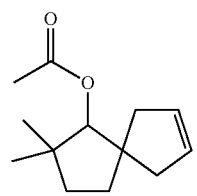

(8,8-dimethylspiro[4.4]non-2-en-9-yl) acetate

In some aspects, the following compound is an inhibitor of the at least one butyric (Compound 23)

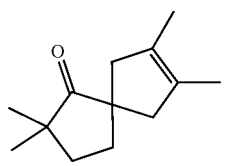

2,3,8,8-tetramethylspiro[4.4]non-2-en-9-one

In some aspects, the following compound is an inhibitor of the at least one butyric acid olfactory receptor:

(Compound 24)

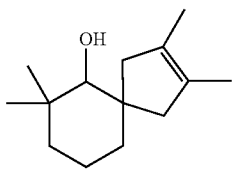

2,3,9,9-tetramethylspiro[4.5]dec-2-en-10-ol

In some aspects, the following compound is an inhibitor of the at least one butyric acid olfactory receptor:

(Compound 25)

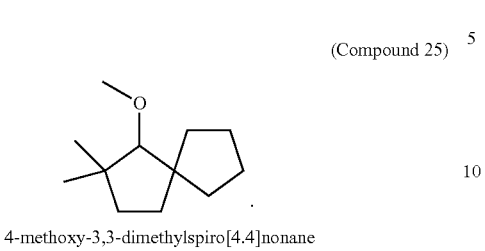

4-methoxy-3,3-dimethylspiro[4.4]nonane

In some aspects, the following compound is an inhibitor of the at least one butyric (Compound 26)

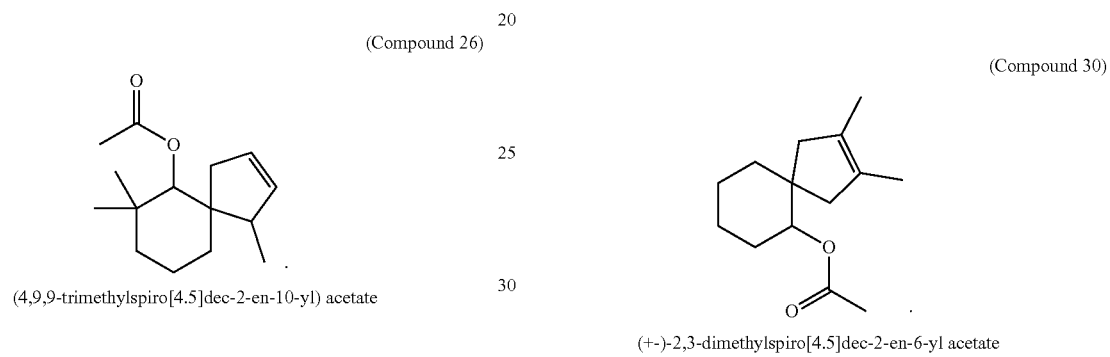

(4,9,9-trimethylspiro[4.5]dec-2-en-10-yl) acetate

In some aspects, the following compound is an inhibitor of the at least one butyric (Compound 27)

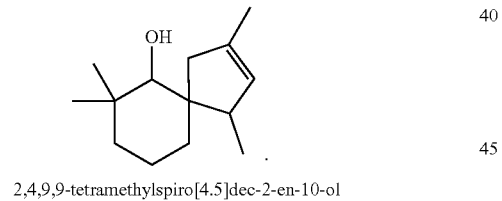

2,4,9,9-tetramethylspiro[4.5]dec-2-en-10-ol

In some aspects, the following compound is an inhibitor of the at least one butyric acid olfactory receptor:

(Compound 28)

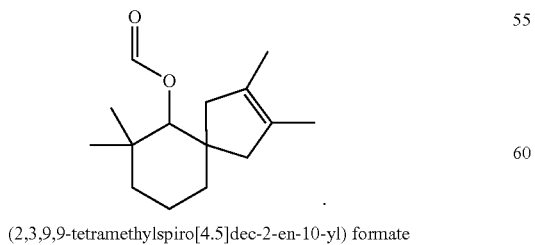

(2,3,9,9-tetramethylspiro[4.5]dec-2-en-10-yl) formate

In some aspects, the following compound is an inhibitor of the at least one butyric acid olfactory receptor.

(Compound 29)

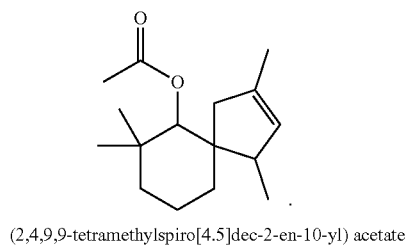

(2,4,9,9-tetramethylspiro[4.5]dec-2-en-10-yl) acetate

In some aspects, the following compound is an inhibitor of the at least one butyric acid olfactory receptor.

(Compound 30)

(+-)-2,3-dimethylspiro[4.5]dec-2-en-6-yl acetate

In some aspects, the following compound is an inhibitor of the at least one butyric acid olfactory receptor.

(Compound 31)

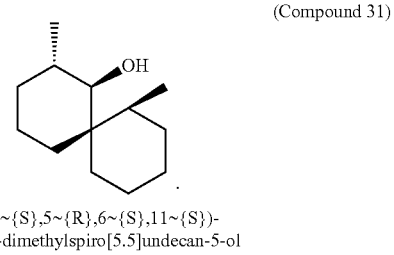

(4~{S},5~{R},6~{S},11~{S})-4,11-dimethylspiro[5.5]undecan-5-ol

In some aspects, the following compound is an inhibitor of the at least one butyric acid olfactory receptor.

(Compound 32)

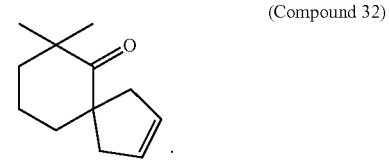

9,9-dimethylspiro[4.5]dec-2-en-10-one

In some aspects, the following compound is an inhibitor of the at least one butyric

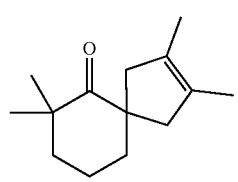

(Compound 33)

2,3,9,9-tetramethylspiro[4.5]dec-2-en-10-one

In some aspects, the following compound is an inhibitor of the at least one butyric acid olfactory receptor:

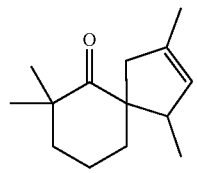

(Compound 34)

2,4,9,9-tetramethylspiro[4.5]dec-2-en-10-one

In some aspects, the following compound is an inhibitor of the at least one butyric acid olfactory receptor:

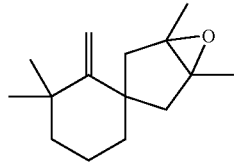

(Compound 35)

1,1′1′,5-tetramethyl-2′-methylidenespiro[6-oxabicyclo[3.1.0]hexane-3,3′-cyclohexane].

In some aspects, the following compound is an inhibitor of the at least one butyric

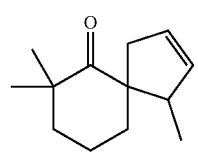

(Compound 36)

4,9,9-trimethylspiro[4.5]dec-2-en-10-one .

In some aspects, the following compound is an inhibitor of the at least one butyric

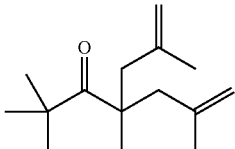

(Compound 37)

2,2-dimethyl-6,-6-bis(2-methylprop-2-enyl)cyclohexan-1-one .

In some aspects, the following compound is an inhibitor of the at least one butyric acid olfactory receptor.

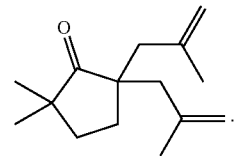

(Compound 38)

2,2-dimethyl-5,5-bis(2-methylprop-2-enyl) cyclopentan-1-one

In some aspects, the following compound is an inhibitor of the at least one butyric acid olfactory receptor.

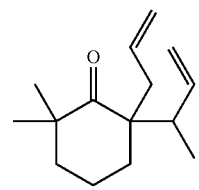

(Compound 39)

2-but-3-en-2-yl-6,6-dimethyl-2-prop-2-enylcyclohexan-1-one .

In some aspects, the following compound is an inhibitor of the at least one butyric

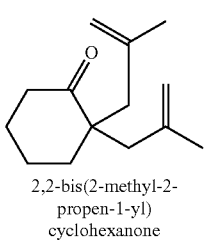

(Compound 40)

2,2-bis(2-methyl-2-propen-1-yl) cyclohexanone .

In some aspects, the following compound is an inhibitor of the at least one butyric acid olfactory receptor.

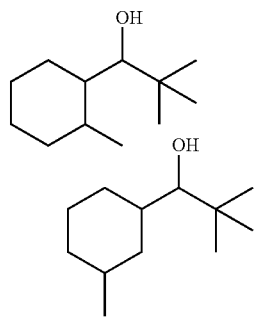

2,2-dimethyl-1-(2-methylcyclohexyl)
propan-1-ol, 2,2-dimethyl-1-(3-
methylcyclohexyl)propan-1-ol,
or mixtures thereof In some aspects, the following compound is an inhibitor of the at least one butyric acid olfactory receptor.

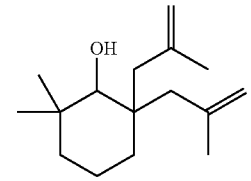

2,2-dimethyl-6,6-bis
(2-methylprop-2-enyl)
cyclohexan-1-ol

In some aspects, the following compound is an inhibitor of the at least one butyric acid olfactory receptor.

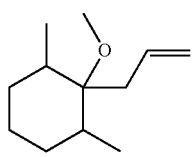

1-methoxy-2,6-
dimethyl-1-prop-2-
enylcyclohexane

In some aspects, the following compound is an inhibitor of the at least one butyric acid olfactory receptor.

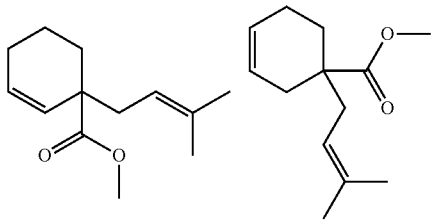

methyl 1-(3-methylbut-2-enyl)cyclohex-2-ene-1-
carboxylate, methyl 1-(3-methylbut-2-enyl)
cyclohex-3-ene-1-carboxylate, or mixtures thereof In some aspects, the following compound is an inhibitor of the at least one butyric acid olfactory receptor.

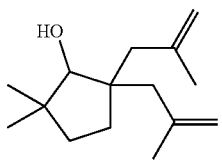

2,2-dimethyl-5,5-
bis(2-methylprop-2-
enyl)cyclopentan-1-ol

Methods to Counteract and/or Mask Malodors According to Some Aspects Presented Herein Some aspects presented herein provide a method,
wherein the method reduces, prevents, or inhibits a subject's perception of malodor,
wherein the method comprises contacting the subject with at least one compound selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl) acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl) acetate, (9,9-dimethylspiro[4.5]dec-2-en-10-yl) acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol, [2,2-dimethyl-1-(2,4,6-trimethylcyclohex-3-en-1-yl) propyl]acetate, [2,2-dimethyl-1-(2,4,6-trimethylcyclohexyl) propyl]acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], 4,9,9-trimethylspiro[4.5]dec-2-en-10-one, 2,2-dimethyl-6,6-bis(2-methylprop-2-enyl) cyclohexan-1-one, 2,2-dimethyl-5,5-bis(2-methylprop-2-enyl) cyclopentan-1-one, 2-but-3-en-2-yl-6,6-dimethyl-2-prop-2-enylcyclohexan-1-one, 2,2-bis(2-methyl-2-propen-1-yl) cyclohexanone, a mixture of 2-but-3-en-2-yl-6,6-dimethyl-2-prop-2-enylcyclohexan-1-one and 2,2-bis(2-methyl-2-propen-1-yl) cyclohexanone, 2,2-dimethyl-1-(2-methylcyclohexyl) propan-1-ol, 2,2-dimethyl-1-(3-methylcyclohexyl) propan-1-ol, a mixture of 2,2-dimethyl-1-(2-methylcyclohexyl) propan-1-ol and 2,2-dimethyl-1-(3-methylcyclohexyl) propan-1-ol, 2,2-dimethyl-6,6-bis(2-methylprop-2-enyl) cyclohexan-1-ol, 1-methoxy-2,6-dimethyl-1-prop-2-enylcyclohexane, methyl 1-(3-methylbut-2-enyl) cyclohex-2-ene-1-carboxylate, methyl 1-(3-methylbut-2-enyl) cyclohex-3-ene-1-carboxylate, a mixture of methyl 1-(3-methylbut-2-enyl) cyclohex-2-ene-1-carboxylate and methyl 1-(3-methylbut-2-enyl) cyclohex-3-ene-1-carboxylate, 2,2-dimethyl-5,5-bis(2-methylprop-2-enyl) cyclopentan-1-ol, 1-(2,6-dimethylcyclohex-3-en-1-yl)-2,2-dimethylpropan-1-ol, and mixtures thereof, wherein the subject is contacted with the at least one compound in an amount sufficient to reduce, prevent, or inhibit the subject's perception of malodor.

Some aspects presented herein provide a method wherein the method inhibits at least one butyric acid receptor in a subject in need thereof, wherein the method comprises contacting the subject with at least one compound selected from the group consisting of: (1RS,6RS,11RS)-2,2,9,11-tetramethylspiro[5.5]undec-8-en-1-yl acetate, (+−)-2,2,7,11-tetramethylspiro[5.5]undec-8-en-1-yl-acetate, (+−)-2,3,7,7-tetramethylspiro[4.5]dec-2-en-6-yl acetate, (+−)-2,3,7,7-tetramethylspiro[4.5]dec-6-yl acetate, 1,5,10,10-tetramethylspiro[5.5]undec-3-en-11-yl acetate, 2,3,9,9-tetramethylspiro[4.5]decan-10-yl) acetate, (5,10,10-trimethylspiro[5.5]undec-2-en-11-yl) formate, (3,5,10,10-tetramethylspiro[5.5]undec-2-en-11-yl) acetate, (2,3,9,9-tetramethylspiro[4.5]dec-2-en-10-yl) acetate, (9,9-dimethylspiro[4.5]dec-2-en-10-yl) acetate, 10-methoxy-9,9-dimethylspiro[4.5]dec-2-ene, 4,10,10,11-tetramethylspiro[5.5]undec-2-en-11-ol, 5,10,10,11-tetramethylspiro[5.5]undec-3-en-11-ol, a mixture of 4,10,10,11-tetramethylspiro[5.5]undec-2-en-11-ol and 5,10,10,11-tetramethylspiro[5.5]undec-3-en-11-ol, 2,4,8-trimethylspiro[5.5]undec-3-en-11-ol, 2,9,11-trimethylspiro[5.5]undec-9-en-5-ol, a mixture of 2,4,8-trimethylspiro[5.5]undec-3-en-11-ol and 2,9,11-trimethylspiro[5.5]undec-9-en-5-ol, 3-methyl-5-propan-2-ylspiro[5.5]undec-2-en-11-ol, 11-methylspiro[5.5]undecan-5-ol, 3,10,10-trimethylspiro[5.5]undec-3-en-11-ol, 4,10,10-trimethylspiro[5.5]undec-3-en-11-ol, a mixture of 3,10,10-trimethylspiro[5.5]undec-3-en-11-ol and 4,10,10-trimethylspiro[5.5]undec-3-en-11-ol, [2,2-dimethyl-1-(2,4,6-trimethylcyclohex-3-en-1-yl) propyl]acetate, [2,2-dimethyl-1-(2,4,6-trimethylcyclohexyl) propyl]acetate, (1RS)-2,2-dimethyl-1-[(1SR,2SR)-2-methylcyclohexyl]propyl acetate, 9,9-dimethylspiro[4.5]dec-2-en-10-ol, 2,3,9,9-tetramethylspiro[4.5]decan-10-ol, (2,2,3,3,9,9-hexamethylspiro[4.5]decan-10-yl) acetate, 9-methoxy-8,8-dimethylspiro[4.4]non-2-ene, (8,8-dimethylspiro[4.4]non-2-en-9-yl) acetate, 2,3,8,8-tetramethylspiro[4.4]non-2-en-9-one, 2,3,9,9-tetramethylspiro[4.5]dec-2-en-10-ol, 4-methoxy-3,3-dimethylspiro[4.4]nonane, (4,9,9-trimethylspiro[4.5]dec-2-en-10-yl) acetate, 2,4,9,9-tetramethylspiro[4.5]dec-2-en-10-ol, (2,3,9,9-tetramethylspiro[4.5]dec-2-en-10-yl) formate, (2,4,9,9-tetramethylspiro[4.5]dec-2-en-10-yl) acetate, (+−)-2,3-dimethylspiro[4.5]dec-2-en-6-yl acetate, (4~{S},5~{R},6~{S},11~{S})-4,11-dimethylspiro[5.5]undecan-5-ol, 9,9-dimethylspiro[4.5]dec-2-en-10-one, 2,3,9,9-tetramethylspiro[4.5]dec-2-en-10-one, 2,4,9,9-tetramethylspiro[4.5]dec-2-en-10-one, 1,1',1',5-tetramethyl-2'-methylidenespiro[6-oxabicyclo[3.1.0]hexane-3,3'-cyclohexane], 4,9,9-trimethylspiro[4.5]dec-2-en-10-one, 2,2-dimethyl-6,6-bis(2-methylprop-2-enyl) cyclohexan-1-one, 2,2-dimethyl-5,5-bis(2-methylprop-2-enyl) cyclopentan-1-one, 2-but-3-en-2-yl-6,6-dimethyl-2-prop-2-enylcyclohexan-1-one, 2,2-bis(2-methyl-2-propen-1-yl) cyclohexanone, a mixture of 2-but-3-en-2-yl-6,6-dimethyl-2-prop-2-enylcyclohexan-1-one and 2,2-bis(2-methyl-2-propen-1-yl) cyclohexanone, 2,2-dimethyl-1-(2-methylcyclohexyl) propan-1-ol, 2,2-dimethyl-1-(3-methylcyclohexyl) propan-1-ol, a mixture of 2,2-dimethyl-1-(2-methylcyclohexyl) propan-1-ol and 2,2-dimethyl-1-(3-methylcyclohexyl) propan-1-ol, 2,2-dimethyl-6,6-bis(2-methylprop-2-enyl) cyclohexan-1-ol, 1-methoxy-2,6-dimethyl-1-prop-2-enylcyclohexane, methyl 1-(3-methylbut-2-enyl) cyclohex-2-ene-1-carboxylate, methyl 1-(3-methylbut-2-enyl) cyclohex-3-ene-1-carboxylate, a mixture of methyl 1-(3-methylbut-2-enyl) cyclohex-2-ene-1-carboxylate and methyl 1-(3-methylbut-2-enyl) cyclohex-3-ene-1-carboxylate, 2,2-dimethyl-5,5-bis(2-methylprop-2-enyl) cyclopentan-1-ol, 1-(2,6-dimethylcyclohex-3-en-1-yl)-2,2-dimethylpropan-1-ol, and mixtures thereof, wherein the subject is contacted with the at least one compound in an amount sufficient to inhibit the at least one butyric acid receptor.

Some aspects described herein provide a method of reducing, preventing, or inhibiting a subject's perception of malodor, comprising contacting the subject with at least one compound selected from the group consisting of: a compound of Formula (I), a compound of Formula (II), a compound of Formula (III), a compound of Formula (IV), and mixtures thereof, in an amount sufficient to reduce, prevent, or inhibit the subject's perception of malodor.

In some aspects, the subject is contacted by treating a surface with, or dispensing at least partly in the air, the at least one compound selected from the group consisting of:

a compound of Formula (I), a compound of Formula (II), a compound of Formula (III), a compound of Formula (IV), and mixtures thereof.

In some aspects, the malodor is selected from the group consisting of: latrine malodor, laundry malodor, and sweat malodor. In some aspects, the malodor contains butyric acid.

In some aspects, the amount sufficient to reduce, prevent, or inhibit the subject's perception of malodor is from 10 to 100 ppm.

In some aspects, the amount sufficient to reduce, prevent, or inhibit the subject's perception of malodor is from 20 to 100 ppm. In some aspects, the amount sufficient to reduce, prevent, or inhibit the subject's perception of malodor is from 30 to 100 ppm. In some aspects, the amount sufficient to reduce, prevent, or inhibit the subject's perception of malodor is from 40 to 100 ppm. In some aspects, the amount sufficient to reduce, prevent, or inhibit the subject's perception of malodor is from 50 to 100 ppm. In some aspects, the amount sufficient to reduce, prevent, or inhibit the subject's perception of malodor is from 60 to 100 ppm. In some aspects, the amount sufficient to reduce, prevent, or inhibit the subject's perception of malodor is from 70 to 100 ppm. In some aspects, the amount sufficient to reduce, prevent, or inhibit the subject's perception of malodor is from 80 to 100 ppm. In some aspects, the amount sufficient to reduce, prevent, or inhibit the subject's perception of malodor is from 90 to 100 ppm.

In some aspects, the amount sufficient to reduce, prevent, or inhibit the subject's perception of malodor is from 10 to 90 ppm. In some aspects, the amount sufficient to reduce, prevent, or inhibit the subject's perception of malodor is from 10 to 80 ppm. In some aspects, the amount sufficient to reduce, prevent, or inhibit the subject's perception of malodor is from 10 to 70 ppm. In some aspects, the amount sufficient to reduce, prevent, or inhibit the subject's perception of malodor is from 10 to 60 ppm. In some aspects, the amount sufficient to reduce, prevent, or inhibit the subject's perception of malodor is from 10 to 50 ppm. In some aspects, the amount sufficient to reduce, prevent, or inhibit the subject's perception of malodor is from 10 to 40 ppm. In some aspects, the amount sufficient to reduce, prevent, or inhibit the subject's perception of malodor is from 10 to 30 ppm. In some aspects, the amount sufficient to reduce, prevent, or inhibit the subject's perception of malodor is from 10 to 20 ppm.

In some aspects, the amount of the at least one compound selected from the group consisting of: a compound of Formula (I), a compound of Formula (II), a compound of Formula (III), a compound of Formula (IV), and mixtures thereof that is effective to inhibit the activity of malodor olfactory receptors is calculated using the $IC_{50}$ value, as determined using a receptor-based assay. In some aspects, the amount of the at least one compound selected from the group consisting of: a compound of Formula (I), a compound of Formula (II), a compound of Formula (III), a compound of Formula (IV), and mixtures thereof that is effective to inhibit the activity of malodor olfactory receptors ranges from 10 to 100 ppm in solution.

Non-limiting examples of kitchen malodor include any type of malodor present in a residential or commercial kitchen including, but not limited to: kitchen garbage odors that may result from the disposal of raw or cooked meat, fish, vegetables, fruit and/or dairy products: odors experienced during food preparation, especially odors generated from raw fish, raw garlic and raw onions: cooking odors, especially odors produced when cooking meat, fish, onion and/or garlic: the odor of cooking oil used for frying foods: burnt odors that may originate from the over-cooking or burning of foods: odors originating from the kitchen sink drain: odors originating from in-sink disposal units; and, odors originating from a refrigerator.

Non-limiting examples of bathroom or latrine malodor include any malodor type of malodor present in a residential or public bathroom/restroom including, but not limited to: odors present immediately after the use of the toilet: lingering toilet odors: stale urine odor; and, moldy or musty odors that often originate in damp areas of the bathroom such as around the bath or shower.

Non-limiting examples of tobacco odor include the odor generated during smoking of cigarettes, cigars or tobacco pipes, or the stale smoke odor that lingers after use of tobacco products in a room, or the odor originating from an ash tray that comprises debris from cigarettes, cigars or tobacco pipes.

Non-limiting examples of pet odor include any type of odor associated with a domestic pet, especially a cat or a dog, and includes, but is not limited to: fecal odors from litter boxes: urine odors from litter boxes: lingering urine odors: wet-dog odor; and, pet-bed odor.

Non-limiting examples of body malodor include any type of odor produced by the human body including, but not limited to: axillary (armpit) odor, scalp odor, foot odor and vaginal odor. "Body malodor" may also mean an odor that originates on the human body and is transferred to another substrate such as a textile: this may include, for example, the odor of worn socks, or the odor of worn sportswear.

Non-limiting examples of laundry malodor include soils such as those found on mechanics' clothes: food handlers, especially butchers' and kitchen workers' clothes: sewer workers' clothes: bar tenders' clothes: fire fighters' clothes: farm clothes: athletic clothing: factory workers' clothes: heavy machinery operators' clothes, mold, odors found in laundry machines, and the like.

Without intending to be limited to any particular theory, residential, body, or laundry malodors are typically due to various malodor targets such as indole, skatole, dimethyl trisulfide, dimethyl disulfide, methanethiol, and butyric acid, found in feces malodor: piperidine and morpholine found in urine: pyridine and triethyl amine found in kitchen and garbage malodors; and short chain fatty acids, such as 3-methyl-3-hydroxyhexanoic acid, 3-methylhexanoic acid, butyric acid, or 3-20 methyl-2-hexenoic acid, found in axillary malodors. As used herein, "malodor target" is meant to designate a molecular component of fecal malodor, sweat malodor, or laundry malodor.

In some aspects, malodor target is butyric acid in the latrine malodor described in Lin et al, Environ. Sci. Technol., 2013, 47 (14), pp 7876-7882.

In some aspects, malodor target is butyric acid in the latrine malodor described in Chappuis et al, Environ. Sci. Technol., 2015, 49 (10), pp 6134-6140.

In some aspects, malodor target is butyric acid in the latrine malodor described in Yasuhara, Chemosphere, 1980, 9 (9), pp 587-592.

In some aspects, malodor target is butyric acid in the body malodor described in Gabbanini et al, Skin Res. & Technol, 2009, 15 (4), pp 503-510.

In some aspects, malodor target is butyric acid in the body malodor described in Gallager et al, B. J. Dermatol., 2008, 159 (4), pp 780-791.

In some aspects, malodor target is butyric acid in the laundry malodor described in McQueen et al, J. Textile Inst., 2008, 99 (6), pp 515-523.

In some aspects, malodor target is butyric acid in the malodor described in Susya et al, Atmospheric Environment, 2011, 45 (6), pp 1236-1241.

In some aspects, malodor target is butyric acid in the oral malodor described in Van den Velds et al, J. Dental Res., 2009, 88 (3), pp 285-289.

In some aspects, the effective amount of the at least one compound selected from the group consisting of: a compound of Formula (I), a compound of Formula (II), a compound of Formula (III), a compound of Formula (IV), and mixtures thereof decreases, suppresses, reduces, or inhibits a subject's perception of the malodor by antagonizing an olfactory malodor receptor, thereby inhibiting the relevant malodor olfactory receptor or relevant malodor olfactory receptors. In some aspects, the olfactory malodor receptor is a butyric acid olfactory receptor. In some aspects, the butyric acid olfactory receptor is OR51E1. Accordingly, in the aspects where the malodor contains butyric acid as a malodor target, inhibition of a subject's butyric acid olfactory receptor may result in the reduction, prevention, or inhibition of the subject's perception of the malodor.

In some aspects, the term "contacting" refers to administering to a subject, a composition comprising at least one compound selected from the group consisting of: a compound of Formula (I), a compound of Formula (II), a compound of Formula (III), a compound of Formula (IV), and mixtures thereof as described herein, wherein the administering results in dosing the subject with an effective amount of the at least one compound selected from the group consisting of: a compound of Formula (I), a compound of Formula (II), a compound of Formula (III), a compound of Formula (IV), and mixtures thereof. Administration may be via any method readily selected by one of ordinary skill in the art. Methods include, but are not limited to, topical administration, inhalation, and the like. Accordingly the present disclosure contemplates formulating a composition comprising a compound of Formula (I) as described herein with a suitable carrier to facilitate administering the a composition comprising at least one compound selected from the group consisting of: a compound of Formula (I), a compound of Formula (II), a compound of Formula (III), a compound of Formula (IV), and mixtures thereof as described herein to the subject.

Alternatively, in some aspects, the term "contacting" refers to dispensing or dispersing a composition comprising at least one compound selected from the group consisting of: a compound of Formula (I), a compound of Formula (II), a compound of Formula (III), a compound of Formula (IV), and mixtures thereof as described herein into a volume in need thereof, wherein the dispensing or dispersing results in dosing the subject with an effective amount of the at least one compound selected from the group consisting of: a compound of Formula (I), a compound of Formula (II), a compound of Formula (III), a compound of Formula (IV), and mixtures thereof. Dispersion or dispensing of the compound of Formula (I) as described herein may be achieved by any method readily selected by one of ordinary skill in the art. Examples include, but are not limited to, a spray, a nebulizer, evaporation of a solution containing at least one compound selected from the group consisting of: a compound of Formula (I), a compound of Formula (II), a compound of Formula (III), a compound of Formula (IV), and mixtures thereof as described herein, and the like.

Accordingly the present disclosure contemplates formulating a composition comprising at least one compound selected from the group consisting of: a compound of Formula (I), a compound of Formula (II), a compound of Formula (III), a compound of Formula (IV), and mixtures thereof as described herein with a suitable carrier to facilitate treating a surface or volume with a composition comprising at least one compound selected from the group consisting of: a compound of Formula (I), a compound of Formula (II), a compound of Formula (III), a compound of Formula (IV), and mixtures thereof as described herein to the subject.

In some aspects, the term "contacting" refers to contacting a surface of a malodor source with a composition comprising at least one compound selected from the group consisting of: a compound of Formula (I), a compound of Formula (II), a compound of Formula (III), a compound of Formula (IV), and mixtures thereof as described herein, wherein the contacting results in an effective amount of the at least one compound selected from the group consisting of: a compound of Formula (I), a compound of Formula (II), a compound of Formula (III), a compound of Formula (IV), and mixtures thereof being deposited on the surface. A composition comprising at least one compound selected from the group consisting of: a compound of Formula (I), a compound of Formula (II), a compound of Formula (III), a compound of Formula (IV), and mixtures thereof as described herein may be contacted on a surface by any method readily selected by one of ordinary skill in the art. Examples include, but are not limited to, a spray, a wipe, a solution, and the like.

Products and Formulations According to Some Aspects Presented Herein

In some aspects, the present disclosure provides a perfumed consumer product comprising at least one compound selected from the group consisting of: a compound of Formula (I), a compound of Formula (II), a compound of Formula (III), a compound of Formula (IV), and mixtures thereof in an amount sufficient to reduce, prevent, or inhibit the subject's perception of malodor. In some aspects, the perfumed consumer product is selected from the group consisting of: air care products, home care products and laundry care products.

In some aspects, the perfumed consumer product comprising an effective amount of at least one compound selected from the group consisting of: a compound of Formula (I), a compound of Formula (II), a compound of Formula (III), a compound of Formula (IV), and mixtures thereof comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It is understood by a person skilled in the art that the at least one compound selected from the group consisting of: a compound of Formula (I), a compound of Formula (II), a compound of Formula (III), a compound of Formula (IV), and mixtures thereof, as defined herein, may be added into composition described herein in neat form, or in a solvent. Alternatively, the at least one compound selected from the group consisting of: a compound of Formula (I), a compound of Formula (II), a compound of Formula (III), a compound of Formula (IV), and mixtures thereof may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof. Alternatively, the at least one compound selected from the group consisting of: a compound of Formula (I), a compound of Formula (II), a compound of Formula (III), a compound of Formula (IV), and mixtures thereof may be chemically bound to substrates which are adapted to release the compounds upon application of an exogenous stimulus such as light, enzymes, or the like.

Accordingly, some aspects presented herein provide a composition comprising:
  a. at least one compound selected from the group consisting of: a compound of Formula (I), a compound of Formula (II), a compound of Formula (III), a compound of Formula (IV), and mixtures thereof;
  b. at least one ingredient selected from the group consisting of a perfumery carrier and a perfumery base; and
  c. optionally at least one perfumery adjuvant.

As used herein, the term "perfumery carrier" refers to a material which is practically neutral from a perfumery point of view, i.e. which does not significantly alter the organoleptic properties of perfuming ingredients. The perfumery carrier may be a liquid or a solid.

Non-limiting examples of liquid perfumery carriers include an emulsifying system, i.e. a solvent and a surfactant system, or a solvent commonly used in perfumery. A detailed description of the nature and type of solvents commonly used in perfumery cannot be exhaustive. However, non-limiting examples solvents include dipropyleneglycol, diethyl phthalate, isopropyl myristate, benzyl benzoate, 2-(2-ethoxyethoxy)-1-ethanol or ethyl citrate.

For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Non-limiting examples of solid perfumery carriers include absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or vet extrusion: or consists of a coating encapsulation, including coacervation and complex coacervation technique.

As used herein, the term "perfumery base" refers a composition comprising at least one perfuming co-ingredient. A perfuming co-ingredient does not include the at least one compound selected from the group consisting of: a compound of Formula (I), a compound of Formula (II), a compound of Formula (III), a compound of Formula (IV), and mixtures thereof. As used herein, the term "perfuming co-ingredient" refers to compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

As used herein, the term "perfumery adjuvant" refers to an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

In some aspects, the composition further comprises a functional perfume accord. As used herein, the term "functional perfume accord" refers to a mixture of at least two perfuming ingredients which possess malodor counteracting properties. For example, the functional perfume accord may comprise a mixture of at least two perfuming ingredients that have been shown to counteract fecal malodor, using a sensory panel.

Non-limiting examples of perfuming ingredients that may be included as functional perfume accords include ionones, irones, damascones, damascenone, citral, methylcinnamic aldehyde, pelargodienal, orivone, or mixtures thereof.

In some aspects, the composition further comprises a non-functional perfume accord.

As used herein, the term "non-functional perfume accord" refers to a mixture of at least two perfuming ingredients which do not possess malodor counteracting properties.

In some aspects, the composition further comprises at least one other MOC compound. As used herein, the term "other MOC compounds" refers to a material which is already known for a MOC activity and is commonly used in the industry for such use. The at least one other MOC compound can be included to further boost, or complement, the MOC activity of the compound of Formula (I).

Non-limiting examples of the at least one other MOC compound include antimicrobial agents, malodor absorbers, chemical neutralisers e.g. acid-base reagents, thiol traps, odour blockers, cross-adaptation agents e.g. as disclosed in U.S. Pat. No. 5,538,719 incorporated herein by reference, malodor complexation agents e.g. various cyclodextrins.

Examples of antimicrobial agents include, but are not limited to, metal salts such as zinc citrate, zinc oxide, zinc pyrethiones, and octopirox: organic acids, such as sorbic acid, benzoic acid, and their salts: parabens, such as methyl paraben, propyl paraben, butyl paraben, ethyl paraben, isopropyl paraben, isobutyl paraben, benzyl paraben, and their salts: alcohols, such as benzyl alcohol, phenyl ethyl alcohol: boric acid: 2,4,4'-trichloro-2-hydroxy-diphenyl ether: phenolic compounds, such as phenol, 2-methyl phenol, 4-ethyl phenol: essential oils such as rosemary, thyme, lavender, eugenol, geranium, tea tree, clove, lemon grass, peppermint, or their active components such as anethole, thymol, eucalyptol, farnesol, menthol, limonene, methyl salicylate, salicylic acid, terpineol, nerolidol, geraniol, and mixtures thereof.

Examples of malodor absorbers include, but are not limited to molecular sieves, such as zeolites, silicas, aluminosilcates, and cyclodextrins; and organic absorbents, such as for example, activated charcoal, dried citrus pulp, cherry pit extract, corncob, and mixtures thereof.

In some aspects, compositions described herein may comprise one, or more than one compound of Formula (I), Formula (II), Formula (III), Formula (IV), or mixtures thereof. Without intending to be limited to any particular theory, a composition comprising more than one compound of Formula (I), Formula (II), Formula (III), Formula (IV), or mixtures thereof may enable a person skilled in the art to prepare MOC compositions possessing an activity finetuned toward the targeted malodor or source of malodor.

For the sake of clarity, it is also understood that any mixture resulting directly from a chemical synthesis, e.g. a reaction medium without an adequate purification, in which at least one compound selected from the group consisting of: a compound of Formula (I), a compound of Formula (II), a compound of Formula (III), a compound of Formula (IV), and mixtures thereof would be involved as a starting, intermediate or end-product could not be considered as a MOC composition according to the present disclosure as far as the mixture does not provide the at least one compound selected from the group consisting of: a compound of Formula (I), a compound of Formula (II), a compound of Formula (III), a compound of Formula (IV), and mixtures thereof in a suitable form. Thus, unpurified reaction mixtures are generally excluded from the present disclosure unless otherwise specified.

Furthermore, at least one compound selected from the group consisting of: a compound of Formula (I), a compound of Formula (II), a compound of Formula (III), a compound of Formula (IV), and mixtures thereof may also be used in any consumer product for which it may be useful to have a MOC activity at least. Consequently, another object of the present disclosure is represented by a MOC consumer product comprising, as an active ingredient, at least one composition, as defined above. It is understood that the MOC consumer product, by its nature can also be a perfuming one.

As used herein, the term "MOC, and optionally perfuming, consumer product" or similar, refers to a consumer product which is expected to deliver at least a MOC effect, and optionally also a pleasant perfuming effect, to the surface to which it is applied (e.g. skin, hair, textile, or home surface, but also air). In other words, a consumer product according to the present disclosure is a perfumed consumer product which comprises the functional formulation, as well as optionally additional benefit agents, corresponding to the desired consumer product, e.g. a detergent or an air freshener, and an effective amount of at least one invention's compound.

The nature and type of the constituents of the MOC consumer product do not warrant a more detailed description here, which in any case would not be exhaustive, the skilled person being able to select them on the basis of his general knowledge and according to the nature and the desired effect of said product.

Non-limiting examples of suitable perfuming consumer product include:

a perfume, such as a fine perfume, an Eau de Toilette, a cologne or an after-shave lotion;

a fabric care product, such as a liquid detergent, a powder detergent, detergent tablets, a detergent bar, a detergent paste, a detergent pouch, a liquid fabric softener, fabric softener sheets, a fabric scent booster, a laundry pretreatment, a fabric refresher, an ironing water, a laundry bleach, a carpet powder or a carpet cleaner;

a hair care product, such as a shampoo, a hair conditioner, a hair cream, a hair oil, a hair styling product (such as a spray, mousse or gel), a hair coloration product or a hair permanent wave product;

a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;

a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;

a skin-cleansing product, such as a soap bar, a shower gel, a liquid hand soap, a bath foam or an intimate wash product;

an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid: a pet-litter.

Some of the above-mentioned MOC consumer products may represent an aggressive medium for the compounds of Formula (I), thus it may be necessary to protect the latter from premature decomposition, for example by encapsulation or by chemically bounding it to another chemical which is suitable to release the invention's ingredient upon a suitable external stimulus, such as an enzyme, light, heat or a change of pH.

In some aspects, the composition as defined in any of the above aspect may be absorbed on a porous or non-porous substrate in loose powder or compacted form, the substrate being selected from cellulose (paper/cardboard), vermiculite, other industrial absorbents, perlite, calcium carbonate, pumice, wood, sawdust, ground corn cob, ground rice hull, rice hull ash, biochars, starches, modified starches and mixtures thereof.

Accordingly, in some aspects, the present disclosure provides a perfumed consumer product comprising an effective amount of at least one compound selected from the group consisting of: a compound of Formula (I), a compound of Formula (II), a compound of Formula (III), a compound of Formula (IV), and mixtures thereof. In some aspects, the perfumed consumer product is selected from the group consisting of: air care products, home care products and laundry care products.

In some aspects, the perfumed consumer product comprising an effective amount of at least one compound selected from the group consisting of: a compound of Formula (I), a compound of Formula (II), a compound of Formula (III), a compound of Formula (IV), and mixtures thereof comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth herein.

The proportions in which at least one compound selected from the group consisting of: a compound of Formula (I), a compound of Formula (II), a compound of Formula (III), a compound of Formula (IV), and mixtures thereof can be incorporated into the various aforementioned products or compositions vary within a wide range of values. These values are dependent on the nature of MOC consumer product and on the desired organoleptic effect as well as the nature of the co-ingredients in a given composition when the compounds of Formula (I) are mixed with other ingredients, solvents or additives commonly used in the art.

In general, for example, in the case of perfuming compositions, typical concentrations are in the order of 0.001% to 5% by weight, or even more, of at least one compound selected from the group consisting of: a compound of Formula (I), a compound of Formula (II), a compound of Formula (III), a compound of Formula (IV), and mixtures thereof, based on the weight of the composition into which they are incorporated. Concentrations lower than these, such as in the order of 0.01% to 100% by weight, can be used when the compositions described herein are incorporated into MOC consumer products, the percentage being relative to the weight of the consumer product.

In particular, the concentration of MOC composition according to the aspects described herein, used in the various aforementioned consumer products varies within a various wide range of values depending on the nature of the consumer product. For instance, a MOC composition according some aspects described herein can be used in a perfume product at a concentration of 0.01% to 50% by weight, alternatively at a concentration of 0.2% to 40% by weight, alternatively at a concentration of 0.5% to 25% by weight. For instance, a MOC composition according to some aspects described herein can be used in a fabric care product at a concentration of 0.01% to 20% by weight, alternatively at a concentration of 0.05% to 10% by weight, alternatively at a concentration of 0.1% to 5% by weight. Yet for instance, a MOC composition according to some aspects described herein can be used in a hair care product at a concentration of 0.01% to 10% by weight, alternatively at a concentration of 0.05% to 5% by weight, alternatively at a concentration of 0.1% to 3% by weight. For instance, a MOC composition according to some aspects described herein can be used in a skin care product at a concentration of 0.01% to 10% by weight, alternatively at a concentration of 0.05% to 5% by weight, most preferably at a concentration of 0.1% to 2.5% by weight. For instance, a MOC composition according to some aspects described herein can be used in a body deodorant or antiperspirant product at a concentration of 0.01% to 10% by weight, alternatively at a concentration of 0.05% to 7% by weight, alternatively at a concentration of 0.1% to 5% by weight. Yet for instance, a MOC composition according to some aspects described herein can be used in a skin cleansing product at a concentration of 0.01% to 5% by weight, alternatively at a concentration of 0.05% to 3% by weight, alternatively at a concentration of 0.1% to 2.5% by weight. For instance, a MOC composition according to some aspects described herein can be used in an air freshening product at a concentration of 0.01% to 100% by weight. For instance, a MOC composition according to some aspects described herein can be used in a surface care product at a concentration of 0.001% to 10% by weight, alternatively at a concentration of 0.01% to 5% by weight, alternatively at a concentration of 0.1% to 2% by weight. Yet, for instance, a MOC composition according to some aspects described herein can be used in a pet-litter product at a concentration of 0.001% to 1% by weight, alternatively at a concentration of 0.005% to 0.5% by weight, alternatively at a concentration of 0.01% to 0.3% by weight.

The present invention is best illustrated but is not limited to the following examples.

EXAMPLES

Example 1: Identification of Butyric Acid Olfactory Receptor Inhibitors

A cell line expressing the OR51E1 olfactory receptor was used as an antagonist screening platform to identify compounds that have the property to decrease the butyric acid induced receptor activity. The cell line was screened with a volatile compound library for their inhibitory properties and potential butyric acid smell inhibition. First, individual binary mixtures of butyric acid with each one of the test compounds were presented to the cells.

Single concentration monitoring of the butyric acid induced cell activity in the presence or absence of a test compound allowed for the identification of compounds with a putative suppression or inhibitory effect. These hits were further confirmed in an inhibitory dose-response assay to evaluate the potency of activity inhibition and efficacy as a measure of the $IC_{50}$ (the inhibitor concentration at which the receptor activity is inhibited by the half-maximal inhibition efficacy level of a given test compound) and % inhibition (normalized to baseline agonist activity) accordingly.

Figure 2:
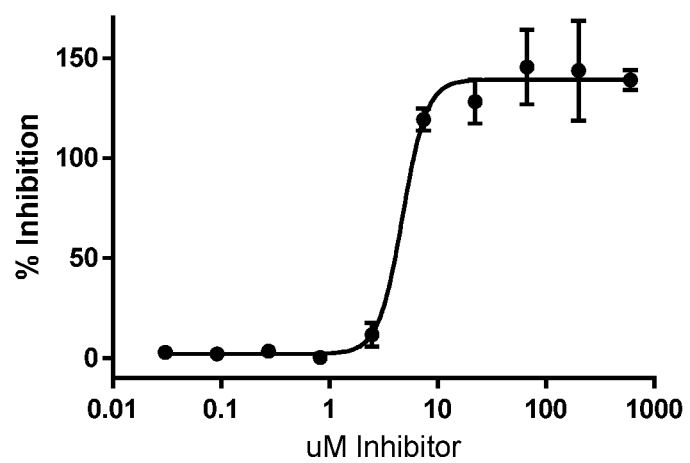
FIG. 2 shows the potency of the antagonist (1,5,10,10-tetramethylspiro[5.5]undec-3-en-11-yl) acetate (Compound 3) as an inhibitor of the butyric acid olfactory receptor OR51E1 under highly stringent screening conditions. The black line denotes the % inhibition of the butyric acid olfactory receptor activity observed from cells treated with 67 μM butyric acid ($EC_{94}$) and the antagonist at the concentrations indicated. The calculated $IC_{50}$ of Compound 3 under these conditions was 4.74 μM.
Figure 3:
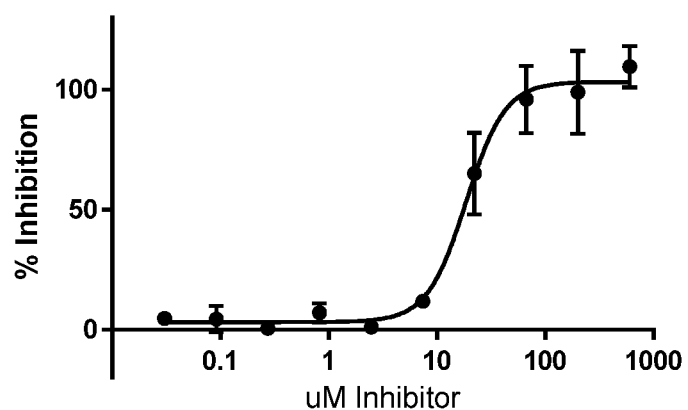
FIG. 3 shows the potency of the antagonist (2,3,9,9-tetramethylspiro[4.5]dec-2-en-10-yl) acetate (Compound 2) as an inhibitor of the butyric acid olfactory receptor OR51E1 under highly stringent screening conditions. The black line denotes the % inhibition of the butyric acid olfactory receptor activity observed from cells treated with 67 μM butyric acid ($EC_{94}$) and the antagonist at the concentrations indicated. The calculated $IC_{50}$ of Compound 2 under these conditions was 18.56 μM.
Figure 4:
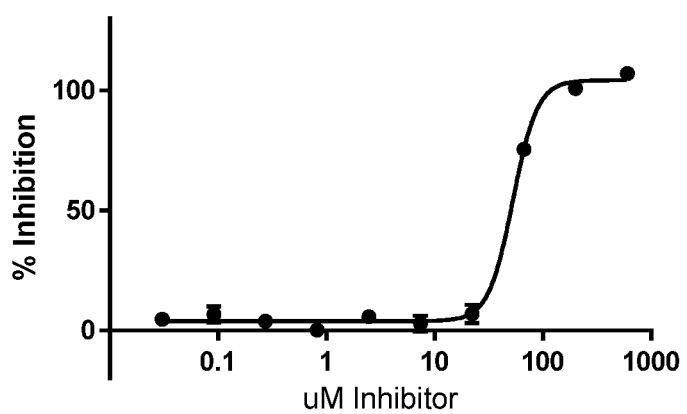
FIG. 4 shows the potency of the antagonist (2,3,9,9-tetramethylspiro[4.5]decan-10-yl) acetate (Compound 4) as an inhibitor of the butyric acid olfactory receptor OR51E1 under highly stringent screening conditions. The black line denotes the % inhibition of the butyric acid olfactory receptor activity observed from cells treated with 67 μM butyric acid and the antagonist at the concentrations indicated ($EC_{94}$). The calculated $IC_{50}$ under these conditions was 52.76 μM.
Figure 5:
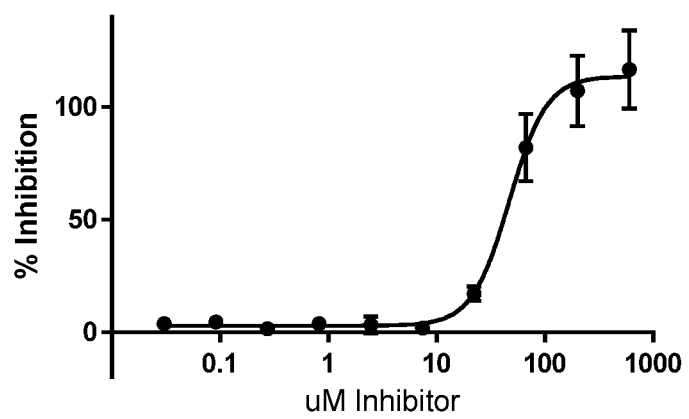
FIG. 5 shows the potency of the antagonist (5,10,10-trimethylspiro[5.5]undec-2-en-11-yl) formate (Compound 5) as an inhibitor of the butyric acid olfactory receptor OR51E1 under highly stringent screening conditions. The black line denotes the % inhibition of the butyric acid olfactory receptor activity observed from cells treated with 67 μM butyric acid ($EC_{94}$) and the antagonist at the concentrations indicated. The calculated $IC_{50}$ of Compound 5 under these conditions was 46.89 μM.
Figure 6:
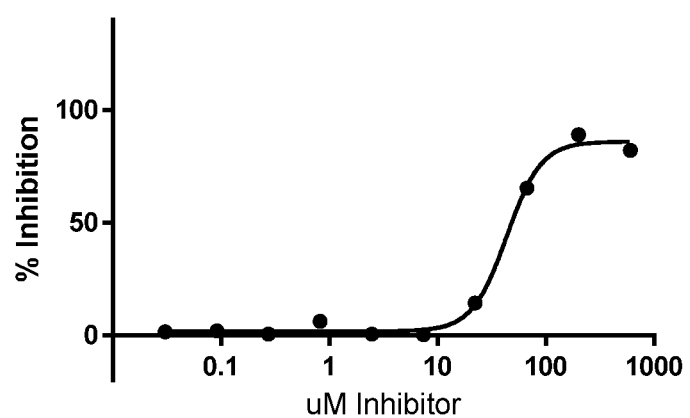
FIG. 6 shows the potency of the antagonist[2,2-dimethyl-1-(2,4,6-trimethylcyclohex-3-en-1-yl) propyl]acetate (Compound 17) as an inhibitor of the butyric acid olfactory receptor OR51E1 under highly stringent screening conditions. The black line denotes the % inhibition of the butyric acid olfactory receptor activity observed from cells treated with 67 μM butyric acid ($EC_{94}$) and the antagonist at the concentrations indicated. The calculated $IC_{50}$ of Compound 17 under these conditions was 43.41 μM.
Figure 7:
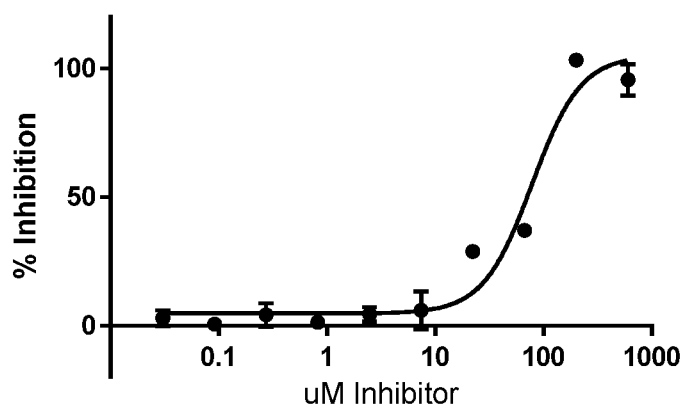
FIG. 7 shows the potency of the antagonist (3,5,10,10-tetramethylspiro[5.5]undec-2-en-11-yl) acetate (Compound 6) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ of Compound 6 under these conditions was 78.11 µM.
Figure 8:
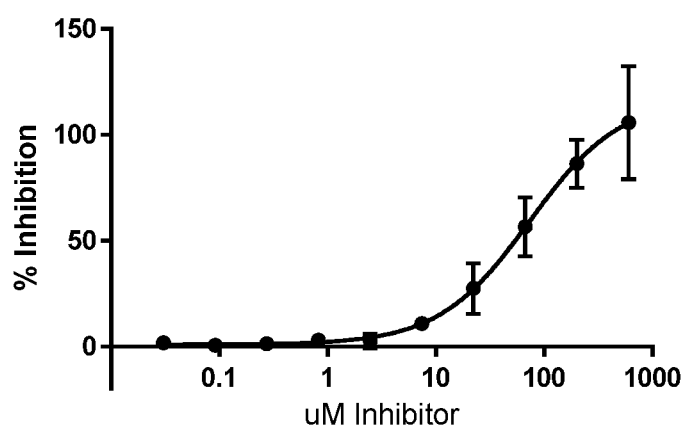
FIG. 8 shows the potency of the antagonist comprising a mixture of 4,10,10,11-tetramethylspiro[5.5]undec-2-en-11-ol and 5,10,10,11-tetramethylspiro[5.5]undec-3-en-11-ol (Compound 9) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ of Compound 9 under these conditions was 73.15 µM.
Figure 9:
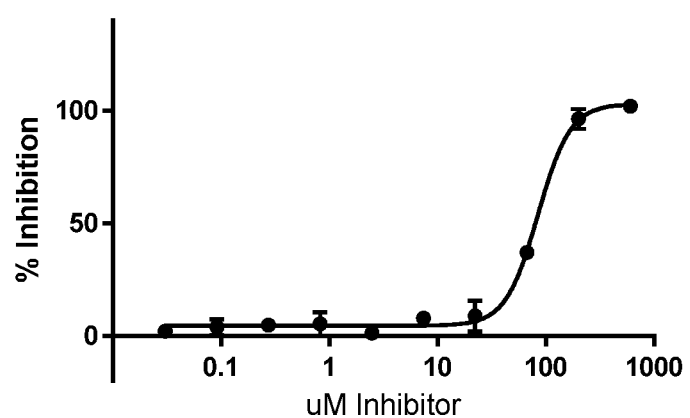
FIG. 9 shows the potency of the antagonist (9,9-dimethylspiro[4.5]dec-2-en-10-yl) acetate (Compound 7) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ of Compound 7 under these conditions was 84.34 µM.
Figure 10:
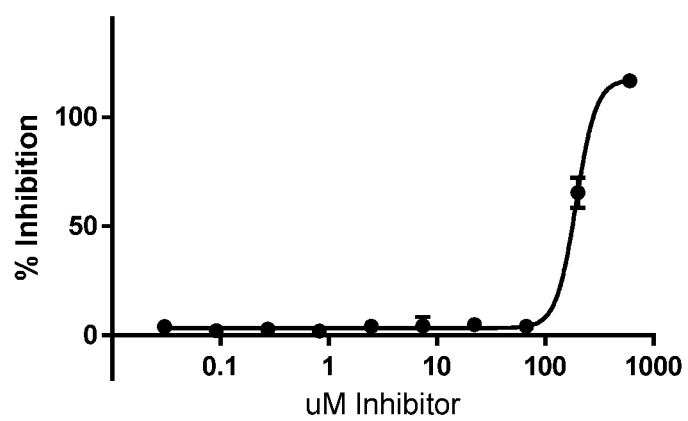
FIG. 10 shows the potency of the antagonist 10-methoxy-9,9-dimethylspiro[4.5]dec-2-ene (Compound 8) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ of Compound 8 under these conditions was 192.50 µM.
Figure 11:
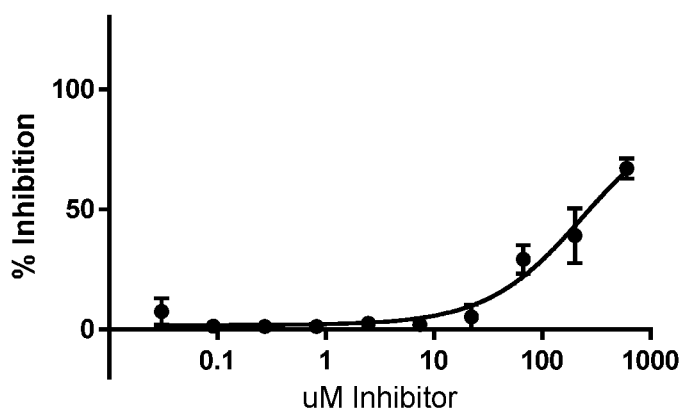
FIG. 11 shows the potency of the antagonist[2,2-dimethyl-1-(2,4,6-trimethylcyclohexyl) propyl]acetate (Compound 15) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ of Compound 15 under these conditions was 237.50 µM.
Figure 12:
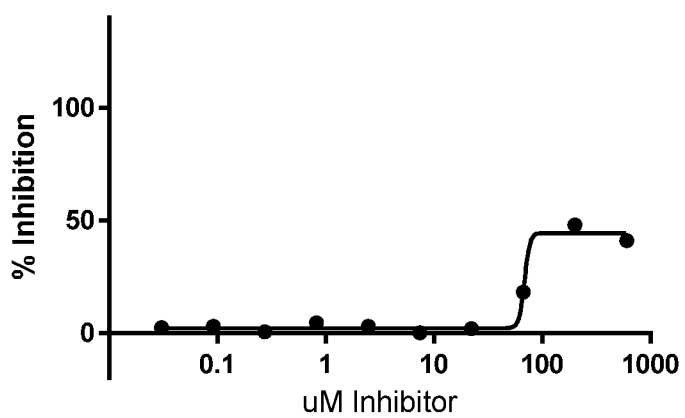
FIG. 12 shows the potency of the antagonist (1RS)-2,2-dimethyl-1-[(1SR,2SR)-2-methylcyclohexyl]propyl acetate (Compound 14) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ of Compound 14 under these conditions was 68.60 µM.
Figure 13:
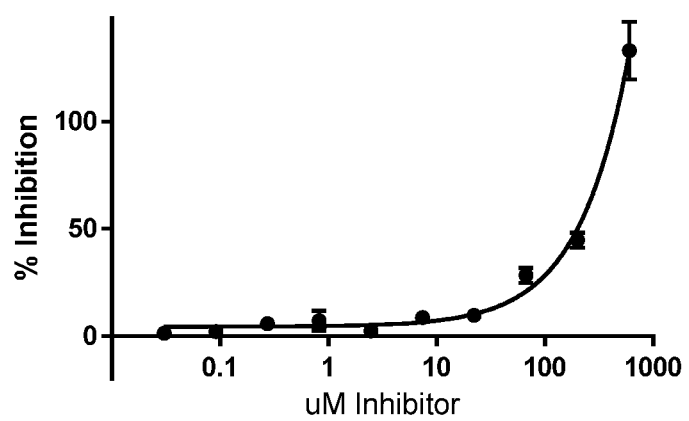
FIG. 13 shows the potency of the antagonist comprising a mixture of 2,4,8-trimethylspiro[5.5]undec-3-en-11-ol and 2,9,11-trimethylspiro[5.5]undec-9-en-5-ol (Compound 10) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The $IC_{50}$ was not calculated.
Figure 14:
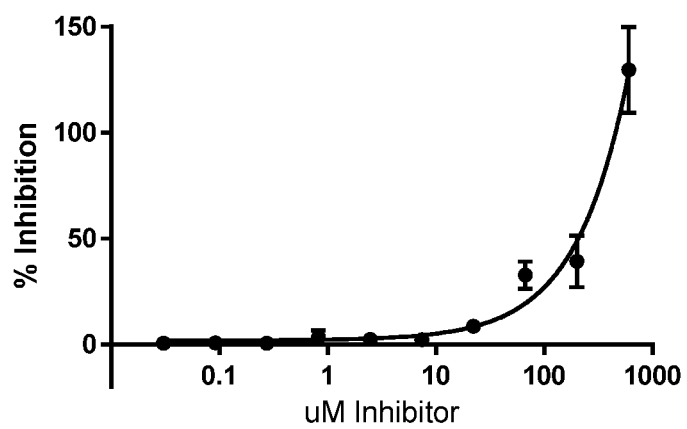
FIG. 14 shows the potency of the antagonist 3-methyl-5-propan-2-ylspiro[5.5]undec-2-en-11-ol (Compound 11) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The $IC_{50}$ was not calculated.
Figure 15:
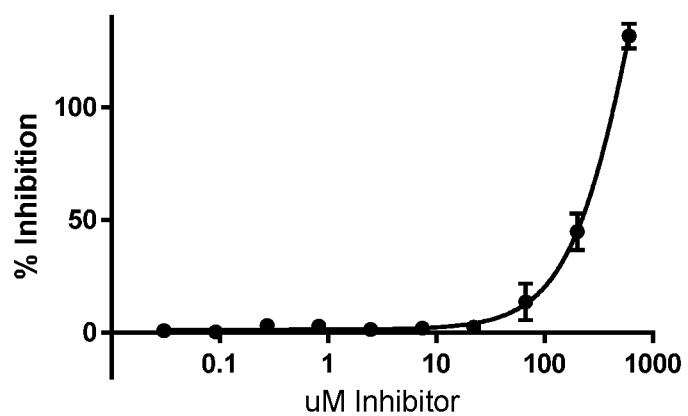
FIG. 15 shows the potency of the antagonist 11-methylspiro[5.5]undecan-5-ol (Compound 12) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ of Compound 12 under these conditions was 804.90 µM.
Figure 16:
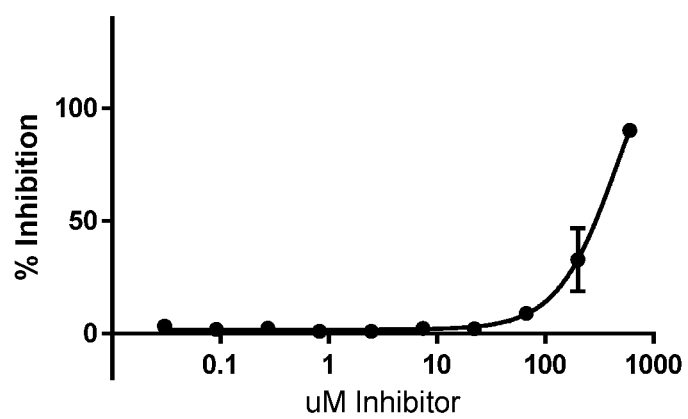
FIG. 16 shows the potency of the antagonist comprising a mixture of 3,10,10-trimethylspiro[5.5]undec-3-en-11-ol and 4,10,10-trimethylspiro[5.5]undec-3-en-11-ol (Compound 13) as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ of Compound 13 under these conditions was 466.10 µM.
Figure 17:
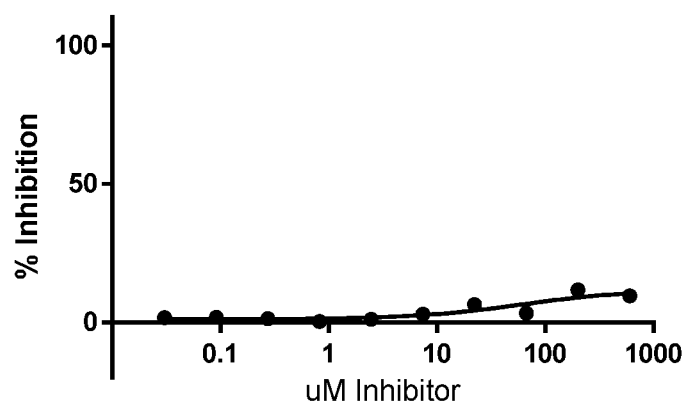
FIG. 17 shows the potency of 1-(2,6-dimethylcyclohex-3-en-1-yl)-2,2-dimethylpropan-1-ol as an inhibitor of the butyric acid olfactory receptor OR51E1 under highly stringent screening conditions. The black line denotes the % inhibition of the butyric acid olfactory receptor activity observed from cells treated with 67 µM butyric acid ($EC_{94}$) and the antagonist at the concentrations indicated. The calculated $IC_{50}$ under these conditions was not calculated.

A dose-dependent decrease of receptor activity was recorded with increasing concentrations of test compounds in the presence of a single activating concentration of butyric acid (for example, $EC_{94}$) and corresponding dose-response inhibition curves were obtained. FIGS. 1 to 16, (showing inhibition curves obtained with butyric acid at $EC_{94}$) and the table below (in which butyric acid was either at $EC_{80}$, $EC_{87}$, $EC_{90}$, or $EC_{100}$) report the activity of compounds according to some aspects of the present invention. The black line in FIGS. 1 to 16 denotes the butyric acid olfactory receptor activity observed from cells treated with the antagonist and butyric acid.

Referring to FIGS. 1 to 16, these data demonstrate that the compounds of Formula (I) are butyric acid olfactory receptor antagonists. However, some compounds performed better than others, as suggested by the relative magnitudes of the inhibition of the butyric acid olfactory receptor. The data in the table below demonstrate that compounds of Formula (I), Formula (II), Formula (III) and Formula (IV) are butyric acid olfactory receptor antagonists, some of which significantly reduced the perception of butyric acid in human sensory tests.

Some of the compounds presented herein demonstrated inverse agonist activity under the conditions described here. Referring to the compounds tested in FIGS. 2, 3, 4, 6, 7, 9, and 11 in particular, these compounds exhibited inverse agonist activity. Without intending to be limited to any particular theory, such compounds may be expected to have a greater malodor counteractant activity.

| IUPAC Name | IC50 | Inhibition (%) | Sensory Performance (%) |
|---|---|---|---|
| (2,3,9,9-tetramethylspiro[4.5]dec-2-en-10-yl) acetate | >600 | 116 | 40% |
| (1,5,10,10-tetramethylspiro[5.5]undec-3-en-11-yl) acetate | 72.33 | 72 | 43% |
| (2,3,9,9-tetramethylspiro[4.5]decan-10-yl) acetate | 51.40 | 62 | 50% |
| (5,10,10-trimethylspiro[5.5]undec-2-en-11-yl) formate | 44.37 | 129 | |
| (3,5,10,10-tetramethylspiro[5.5]undec-2-en-11-yl) acetate | 71.39 | 104 | |
| (9,9-dimethylspiro[4.5]dec-2-en-10-yl) acetate | 90.30 | 32 | |
| 10-methoxy-9,9-dimethylspiro[4.5]dec-2-ene | 119.54 | 33 | |
| 4,10,10,11-tetramethylspiro[5.5]undec-2-en-11-ol, 5,10,10,11-tetramethylspiro[5.5]undec-3-en-11-ol, or mixtures thereof | 47.23 | 94 | |
| 2,4,8-trimethylspiro[5.5]undec-3-en-11-ol, 2,9,11-trimethylspiro[5.5]undec-9-en-5-ol, or mixtures thereof | 117.03 | 70 | |
| 3-methyl-5-propan-2-ylspiro[5.5]undec-2-en-11-ol | 366.37 | 144 | |
| 11-methylspiro[5.5]undecan-5-ol | 68.82 | 52 | |
| 3,10,10-trimethylspiro[5.5]undec-3-en-11-ol, 4,10,10-trimethylspiro[5.5]undec-3-en-11-ol, or mixtures thereof | >600 | 121 | |
| [2,2-dimethyl-1-(2,4,6-trimethylcyclohex-3-en-1-yl)propyl] acetate | 52.56 | 89 | |
| [2,2-dimethyl-1-(2,4,6-trimethylcyclohexyl)propyl] acetate | 241.99 | 101 | |
| [(1~{R})-2,2-dimethyl-1-[(1~{S},2~{S})-2-methylcyclohexyl]propyl] acetate | 169.82 | 86 | |
| 2,3,9,9-tetramethylspiro[4.5]dec-2-en-10-ol | 78.69 | 16 | 60% |
| 2,3,9,9-tetramethylspiro[4.5]dec-2-en-10-one | | | 56% |
| 2,2-dimethyl-6,6-bis(2-methylprop-2-enyl)cyclohexan-1-one | 46.59 | 103 | 50% |
| (2,3,9,9-tetramethylspiro[4.5]dec-2-en-10-yl) formate | 25.90 | 69 | |
| (2,4,9,9-tetramethylspiro[4.5]dec-2-en-10-yl) acetate | 34.79 | 131 | |
| 2,2-dimethyl-5,5-bis(2-methylprop-2-enyl)cyclopentan-1-ol | 35.11 | 119 | |
| 9,9-dimethylspiro[4.5]dec-2-en-10-ol | 44.06 | 91 | |
| (4,9,9-trimethylspiro[4.5]dec-2-en-10-yl) acetate | 48.52 | 106 | |
| 2,2-dimethyl-5,5-bis(2-methylprop-2-enyl)cyclopentan-1-one | 51.71 | 82 | |
| 1,1',1',5-tetramethyl-2'-methylidenespiro[6-oxabicyclo[3.1.0]hexane-3,3'-cyclohexane] | 75.67 | 37 | |
| 2-but-3-en-2-yl-6,6-dimethyl-2-prop-2-enylcyclohexan-1-one | 76.42 | 115 | |
| (4~{S},5~{R},6~{S},11~{S})-4,11-dimethylspiro[5.5]undecan-5-ol | 76.93 | 54 | |
| 2,4,9,9-tetramethylspiro[4.5]dec-2-en-10-ol | 81.58 | 22 | |
| 2,2-dimethyl-1-(2-methylcyclohexyl)propan-1-ol, 2,2-dimethyl-1-(3-methylcyclohexyl)propan-1-ol, or mixtures thereof | 83.27 | 17 | |
| 1-methoxy-2,6-dimethyl-1-prop-2-enylcyclohexane | 100.21 | 61 | |
| 2,4,9,9-tetramethylspiro[4.5]dec-2-en-10-one | 109.82 | 63 | |
| 2,3,9,9-tetramethylspiro[4.5]decan-10-ol | 119.78 | 12 | |

| IUPAC Name | IC50 | Inhibition (%) | Sensory Performance (%) |
|---|---|---|---|
| 2,2-dimethyl-6,6-bis(2-methylprop-2-enyl)cyclohexan-1-ol | 124.71 | 110 | |
| 9,9-dimethylspiro[4.5]dec-2-en-10-one | 135.02 | 23 | |
| 2,3,8,8-tetramethylspiro[4.4]non-2-en-9-one | 198.38 | 10 | |
| 9-methoxy-8,8-dimethylspiro[4.4]non-2-ene | 237.96 | 100 | |
| 4,9,9-trimethylspiro[4.5]dec-2-en-10-one | 267.67 | 102 | |
| 1-(2,6-dimethylcyclohex-3-en-1-yl)-2,2-dimethylpropan-1-ol | 321.14 | 31 | |
| 4-methoxy-3,3-dimethylspiro[4.4]nonane | 337.13 | 105 | |
| (2,2,3,3,9,9-hexamethylspiro[4.5]decan-10-yl) acetate | 424.91 | 39 | |
| (8,8-dimethylspiro[4.4]non-2-en-9-yl) acetate | 488.31 | 107 | |
| methyl 1-(3-methylbut-2-enyl)cyclohex-2-ene-1-carboxylate, methyl 1-(3-methylbut-2-enyl)cyclohex-3-ene-1-carboxylate, or mixtures thereof | 576.63 | 38 | |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A compound, which is selected from the group consisting of: 2,2-dimethyl-6,6-bis(2-methylprop-2-enyl) cyclohexan-1-one, 2,2-dimethyl-5,5-bis(2-methylprop-2-enyl) cyclopentan-1-one, 2-but-3-en-2-yl-6,6-dimethyl-2-prop-2-enylcyclohexan-1-one, and 2,2-bis(2-methyl-2-propen-1-yl) cyclohexanone.

2. A perfuming composition comprising the compound of claim 1.

3. A consumer product comprising the compound of claim 1.

* * * * *